US010588992B2

(12) United States Patent
Frische et al.

(10) Patent No.: US 10,588,992 B2
(45) Date of Patent: Mar. 17, 2020

(54) AEROSOL DEVICE

(71) Applicant: WATERTECH HOLDINGS LLC, Charleston, SC (US)

(72) Inventors: Eric August Frische, Addison, TX (US); Christopher Benedict Spaulding, Charleston, SC (US); Thomas Kurt Klemann, Goose Creek, SC (US)

(73) Assignee: Watertech Holdings LLC, Charleston, SC (US)

( * ) Notice: Subject to any disclaimer, the term of this patent is extended or adjusted under 35 U.S.C. 154(b) by 221 days.

(21) Appl. No.: 15/494,217

(22) Filed: Apr. 21, 2017

(65) Prior Publication Data

US 2017/0304475 A1    Oct. 26, 2017

Related U.S. Application Data

(60) Provisional application No. 62/326,114, filed on Apr. 22, 2016.

(51) Int. Cl.

| *A61L 9/00* | (2006.01) |
| *B05B 1/28* | (2006.01) |
| *B05B 7/10* | (2006.01) |
| *A61L 2/22* | (2006.01) |
| *B05B 7/24* | (2006.01) |
| *A61L 2/24* | (2006.01) |
| *A61L 9/14* | (2006.01) |
| *B05B 7/00* | (2006.01) |

(Continued)

(52) U.S. Cl.
CPC .................. *A61L 2/22* (2013.01); *A61L 2/24* (2013.01); *A61L 9/14* (2013.01); *B05B 7/0075* (2013.01); *B05B 7/2489* (2013.01); *B05B 7/2491* (2013.01); *B65D 83/48* (2013.01); *B65D 83/62* (2013.01); *B65D 83/72* (2013.01); *A61L 2202/14* (2013.01); *A61L 2202/15* (2013.01); *A61L 2202/25* (2013.01); *A61L 2209/11* (2013.01); *A61L 2209/134* (2013.01)

(58) Field of Classification Search
CPC ..... A61L 2/22; A61L 9/16; A61L 9/14; B05B 7/249; B05B 3/02
USPC ........... 422/1, 5, 28, 305–306; 239/403, 291
See application file for complete search history.

(56) References Cited

U.S. PATENT DOCUMENTS

| 2006/0121844 A1* | 6/2006 | Sparks, II ................. A61L 9/14 |
| | | 454/337 |
| 2009/0010800 A1* | 1/2009 | Resch ..................... A61L 2/202 |
| | | 422/4 |

FOREIGN PATENT DOCUMENTS

WO   WO-2015102997 A1 *   7/2015   ............... A61L 2/20

* cited by examiner

*Primary Examiner* — Monzer R Chorbaji
(74) *Attorney, Agent, or Firm* — Meunier Carlin & Curfman LLC

(57) ABSTRACT

An aerosol device having a bowl with a bottom defining a drain, and a side wall extending from the bottom to a rim. A nozzle is disposed within the bowl. The nozzle defines a chamber and an outlet orifice directed toward the side wall of the bowl. The aerosol device includes a liquid container fluidly coupled to the nozzle via a first conduit having an outlet tip disposed within the chamber of the nozzle and a second conduit connecting a source of pressurized gas to the chamber of the nozzle. The outlet tip is in the form of a tube defining elongated slots communicating from inside the tube to outside the tube, the slots each having a width defined between two parallel tube surfaces. The aerosol device generates submicron liquid droplets, and is suitable for disinfecting porous articles in an enclosed volume.

6 Claims, 20 Drawing Sheets

Figure 1A:
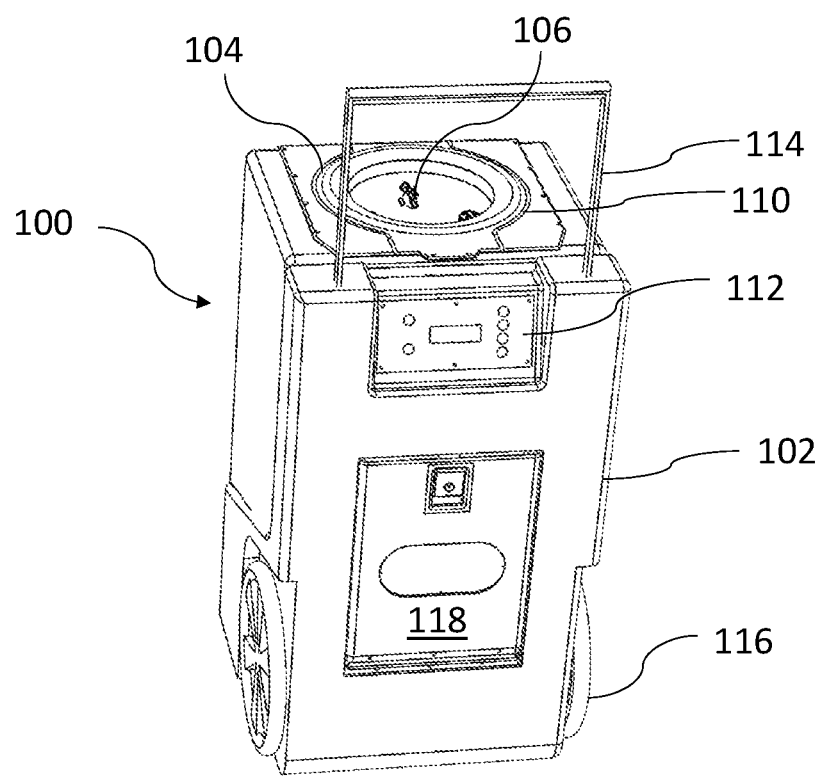

(51) Int. Cl.
*B65D  83/48*    (2006.01)
*B65D  83/62*    (2006.01)
*B65D  83/72*    (2006.01)

1500 → | Assessing an initial relative humidity, an initial ambient temperature, and an initial barometric pressure in a room | — 1502

↓

| Initiating production of an aerosol within the room | — 1504

↓

| Monitoring the relative humidity within the room over time to yield measured values of relative humidity as a function of time | — 1506

↓

| Comparing the measured values of relative humidity to stored reference data | — 1508

↓

| Based on the comparison, determining a treatment parameter of the aerosol in the room | — 1510

↓

| Terminating production of the aerosol within the room after the treatment parameter has been achieved | — 1512

FIG. 15

1600 → | Providing an aerosol to a room, where the aerosol includes liquid droplets and the liquid droplets include a disinfectant | — 1602

↓

| Allowing the liquid droplets to diffuse throughout the room and into porous articles in the room for a sufficient length of time to disinfect the room, where a majority of the liquid droplets have a maximum dimension of 0.1 μm to 0.7 μm | — 1604

FIG. 16

AEROSOL DEVICE

CROSS-REFERENCE TO RELATED APPLICATION

This application claims the benefit of U.S. Provisional Application Ser. No. 62/326,114 entitled "AEROSOL DEVICE" and filed on Apr. 22, 2016, which is incorporated by reference herein in its entirety.

TECHNICAL FIELD

This invention relates to devices, systems, and methods for forming an aerosol.

BACKGROUND

An aerosol is a suspension of liquid or solid particles in a gas. Aerosols are used for a variety of purposes, including delivery of a substance such as a medicinal drug or an insecticide. In some cases, an aerosol is formed with a can or bottle that contains a propellant and a substance to be delivered. Some aerosols are considered to be harmful to the environment. Other aerosols are considered to be an efficient and cost-effective means to deliver a substance to a target area.

SUMMARY

In a first general aspect, an aerosol device includes a bowl with a bottom defining a drain, and a side wall extending from the bottom to a rim. The bottom and the side wall together define an interior surface of the bowl bounding a bowl volume. The aerosol device includes a nozzle disposed within the bowl. The nozzle defines a chamber and an outlet orifice directed toward the side wall of the bowl. The aerosol device includes a liquid container fluidly coupled to the nozzle via a first conduit having an outlet tip disposed within the chamber of the nozzle, and a second conduit connecting a source of pressurized gas to the chamber of the nozzle. The outlet tip is in the form of a tube defining elongated slots communicating from inside the tube to outside the tube, the slots each having a width defined between two parallel tube surfaces.

Implementations of the first general aspect may include one or more of the following features.

Each of the slots may have at least one end formed by two square corners. Each of the slots may have at least one end formed by a radius. Each of the slots may have two closed ends. Each of the slots may be open at an end of the tube or closed at the end of the tube. Each of the slots may have at least one end formed by a radius. Each of the slots may define a longitudinal axis parallel with a longitudinal axis of the tube. A length of each of the slots may form an acute angle with a longitudinal axis of the tube. The tube may have a closed end or an open end at the outlet tip.

In a second general aspect, disinfecting a room comprises providing an aerosol to a room, the aerosol including liquid droplets and the liquid droplets including a disinfectant, and allowing the liquid droplets to diffuse throughout the room and into porous articles in the room for a sufficient length of time to disinfect the room. A majority of the liquid droplets have a maximum dimension in a range between 0.1 μm and 0.7 μm.

Implementations of the second general aspect may include one or more of the following features.

A majority of the liquid droplets may have a maximum dimension in a range between 0.3 μm and 0.7 μm. The porous articles may include cloth. A maximum dimension of a majority of pores in the porous articles may exceed 0.7 μm. The disinfectant may include hypochlorous acid. A concentration of free available chlorine in the liquid droplets may be at least 1800 parts per million by weight.

In a third general aspect, treating a room includes assessing an initial relative humidity, an initial ambient temperature, and an initial barometric pressure in the room; initiating production of an aerosol within the room; monitoring the relative humidity within the room over time to yield measured values of relative humidity as a function of time; comparing the measured values of relative humidity to stored reference data; based on the comparison, determining a treatment parameter of the aerosol in the room; and terminating production of the aerosol within the room after the treatment parameter has been achieved.

Implementations of the third general aspect may include one or more of the following features.

Treating the room may include disinfecting the room. The aerosol may include liquid droplets including a disinfectant. The disinfectant may include hypochlorous acid. A concentration of free available chlorine in the liquid droplets may be at least 1800 parts per million by weight. The aerosol may include liquid droplets having a maximum dimension in a range of 0.1 μm to 0.7 μm or 0.3 μm to 0.7 μm. The treatment parameter may include at least one of a total production time of the aerosol, a total amount of a disinfectant in the aerosol, and a target relative humidity percentage in the room. The stored reference data may include known values of relative humidity as a function of time for a reference room of a known volume in which a reference aerosol is generated at a known initial relative humidity, a known initial ambient temperature, and a known initial barometric pressure.

In a fourth general aspect, an aerosol system includes a bowl including a bottom defining a drain, and a side wall extending from the bottom to a rim. The bottom and the side wall together define an interior surface of the bowl bounding a bowl volume. The aerosol system includes a nozzle disposed within the bowl. The nozzle defines a chamber and an outlet orifice. The aerosol system includes a liquid container fluidly coupled to the nozzle via a first conduit having an outlet tip disposed within the chamber of the nozzle. The liquid container is configured to contain a liquid including a disinfectant. The aerosol system includes a pump configured to pump liquid from the liquid container to the nozzle via the first conduit and a second conduit connecting a source of pressurized gas to the chamber. The aerosol system includes a processor operatively coupled to both the pump and the pressurized gas source and configured to monitor ambient temperature, barometric pressure, and relative humidity of a target volume, and to control both the pump and the pressurized gas source to provide an aerosol to the target volume for a length of time sufficient to achieve a selected treatment parameter.

Implementations of the fourth general aspect may include one or more of the following features.

The selected treatment parameter may include at least one of a total production time of the aerosol, a total amount of a disinfectant in the aerosol, and a target relative humidity percentage in the target volume. The processor may be configured to terminate production of the aerosol after the selected treatment parameter is achieved.

The aerosol system may include a sensor operatively coupled to the processor. The sensor may be a pH sensor, and the processor may be configured to monitor a pH of the liquid. The bowl may include a reservoir proximate the drain, the sensor may be a liquid level sensor, and the processor may be configured to monitor a level of the liquid in the reservoir. The sensor may be a free available chlorine sensor, and the processor may be configured to monitor a concentration of free available chlorine in the liquid. The sensor may be an electrical conductivity sensor, and the processor may be configured to monitor an electrical conductivity of the liquid. The sensor may be an oxidation reduction potential sensor, and the processor may be configured to monitor an oxidation reduction potential of the liquid.

The aerosol system may include a temperature sensor operatively coupled to the processor. The aerosol system may include a relative humidity sensor operatively coupled to the processor. The aerosol system may include a barometric pressure sensor operatively coupled to the processor.

The aerosol system may include a waste container fluidly coupled to the drain.

In a fifth general aspect, an aerosol device includes a bowl including a bottom defining a drain, and a side wall extending from the bottom to a rim. The bottom and the side wall together define an interior surface of the bowl bounding a bowl volume. The aerosol devices includes a nozzle disposed within the bowl, the nozzle defining a chamber and an outlet orifice. The aerosol device includes a liquid container fluidly coupled to the nozzle via a first conduit having an outlet tip disposed within the chamber of the nozzle, and a second conduit connecting a source of pressurized gas to the chamber of the nozzle. The first and second conduits extend into the bowl through the side wall.

Implementations of the fifth general aspect may include one or more of the following features.

The nozzle may include a stem extending through the side wall. The stem may be orthogonal to the side wall or form an oblique angle with the side wall. The stem may form an angle in a range between 20° and 40° with the side wall or between 25° and 35° with the side wall.

The chamber may be a vortidal chamber. The vortical chamber may have a first cylindrical portion, a frustoconical portion, and a second cylindrical portion. The outlet orifice may be proximate the second cylindrical portion. A tip of the first conduit may be positioned in the frustoconical portion of the vortical chamber and define a fluid outlet.

The source of pressurized gas may be a compressor. The second conduit may define a gas outlet.

The aerosol device may include a lip that extends into an interior of the bowl (e.g., extend inwardly from the side wall of the bowl). The lip may be coupled to the side wall of the bowl. The lip may extend at least 0.5 cm into the interior of the bowl. The lip may extend up to 3 cm into the interior of the bowl. The lip may be curved. A cross section of the lip taken perpendicular to the side wall may be concave downward with respect to the bottom of the bowl.

The aerosol device may include a lid configured to engage the rim of the bowl/The lid may define an opening configured to allow an aerosol formed by the nozzle to exit the bowl. The lid may be hingedly or slidably coupled to the bowl. A portion of the lid may extend toward the bottom of the bowl. The nozzle may be contained between the side wall of the bowl and the portion of the lid that extends toward the bottom of the bowl. The portion of the lid that extends toward the bottom of the bowl may define an opening, and an aerosol formed by the nozzle may exit the bowl through the opening.

The fluid outlet may define elongated slots communicating from inside the conduit to outside the conduit, the slots each having a width defined between two parallel tube surfaces. Each of the slots may have at least one end formed by two square corners. Each of the slots may have at least one end formed by a radius. Each of the slots may have two closed ends. Each of the slots may be open at an end of the tube or closed at the end of the tube. Each of the slots may have at least one end formed by a radius. Each of the slots may define a longitudinal axis parallel with a longitudinal axis of the tube. A length of each of the slots may form an acute angle with a longitudinal axis of the tube. The tube may have a closed end or an open end at the outlet tip.

The aerosol device may include a pump configured to provide liquid from the liquid container to the nozzle via the fluid outlet in the first conduit. The aerosol device may include a single nozzle. The aerosol device may include one or more additional nozzles extending inwardly from the side wall of the bowl.

The aerosol device may include a central post disposed within the bowl and having a continuous outer perimeter surface defining an inner boundary of a flow volume within the bowl, the nozzle disposed within the flow volume between the side wall of the bowl and the outer perimeter surface of the post and arranged to generate a flow around the post. The post may be cylindrical. The outer perimeter surface of the post may be tapered, such that the post has a larger perimeter at an end closest to the bottom of the bowl. The side wall of the bowl may be tapered in a similar direction as the outer perimeter surface, such that the side wall generally follows the outer perimeter surface. The post may cover the drain and defines apertures allowing fluid to flow from the flow volume into the drain.

The liquid compartment may include a waste container, and the drain may be fluidly coupled to the waste receptacle.

In a sixth general aspect, an aerosol device includes a bowl with a bottom defining a drain, and a side wall extending from the bottom to a rim. The bottom and the side wall together define an interior surface of the bowl bounding a bowl volume. The aerosol device includes a nozzle disposed within the bowl. The nozzle defines a chamber and an outlet orifice directed toward the side wall of the bowl. The aerosol device includes a liquid container fluidly coupled to the nozzle via a first conduit having an outlet tip disposed within the chamber of the nozzle, a second conduit connecting a source of pressurized gas to the chamber of the nozzle, and a lip extending inward to overhang the side wall about the bowl with the nozzle disposed between the lip and the bottom of the bowl, at least a portion of the nozzle extending radially inward past the lip, the lip defining a bowl outlet opening through which aerosol generated within the bowl passes out of the bowl.

Implementations of the sixth general aspect may include one or more of the following features. The lip may extend at least 0.5 cm into the interior of the bowl. The lip may extend less than 3 cm into the interior of the bowl. An inner region of the lip may curve downward toward the bottom of the bowl.

In a seventh general aspect, an aerosol device includes a bowl with a bottom defining a drain, and a side wall extending from the bottom to a rim. The bottom and the side wall together define an interior surface of the bowl bounding a bowl volume. The aerosol device includes a nozzle disposed within the bowl. The nozzle defines a chamber and an outlet orifice directed toward the side wall of the bowl. The aerosol device includes a liquid container fluidly coupled to the nozzle via a first conduit having an outlet tip disposed within the chamber of the nozzle and a second conduit connecting a source of pressurized gas to the chamber of the nozzle. The aerosol device includes a central post disposed within the bowl and having a continuous outer perimeter surface defining an inner boundary of a flow volume within the bowl. The nozzle is disposed within the flow volume between the side wall of the bowl and the outer perimeter surface of the post and arranged to generate a flow around the post.

Implementations of the seventh general aspect may include one or more of the following features.

The post may be cylindrical. The outer perimeter surface of the post may be tapered, such that the post has a larger perimeter at an end closest to the bottom of the bowl. The side wall of the bowl may be tapered in a similar direction as the outer perimeter surface, such that the side wall generally follows the outer perimeter surface. The post may cover the drain and defines apertures allowing fluid to flow from the flow volume into the drain.

In an eighth general aspect, an aerosol device includes a bowl with a bottom defining a drain, and a side wall extending from the bottom to a rim. The bottom and the side wall together define an interior surface of the bowl bounding a bowl volume. The aerosol device includes a nozzle disposed within the bowl. The nozzle defines a chamber and an outlet orifice directed, projected in a plane perpendicular to the primary longitudinal axis of the bowl, along a chord of a circle defined by the side wall. The aerosol device includes a a liquid container fluidly coupled to the nozzle via a first conduit having an outlet tip disposed within the chamber of the nozzle, and a second conduit connecting a source of pressurized gas to the chamber of the nozzle. A distance between the nozzle outlet orifice and the side wall of the bowl, along the chord and in a spray direction of the nozzle, is less than ⅓ an overall length of the chord.

Described herein is a high-volume, intelligent aerosol device that can cover wide areas and automatically provide an effective aerosol treatment to an area, such as an enclosed volume. In one example, an aerosol device provides complete disinfecting of an area without chemical degradation of the disinfectant and without creating hazardous conditions.

The details of one or more implementations of the subject matter described in this specification are set forth in the accompanying drawings and the following description. Other features, aspects, and advantages of the subject matter will become apparent from the description, the drawings, and the claims.

BRIEF DESCRIPTION OF THE DRAWINGS

FIG. 1A depicts an aerosol device.

FIG. 1B depicts a portion of the aerosol device of FIG. 1A.

FIG. 1C depicts components in the aerosol device of FIG. 1A.

FIG. 2A depicts a bowl of an aerosol device with nozzles that extend inward from a side wall of the bowl.

FIG. 2B is a top view of the bowl of FIG. 2A.

FIG. 2C is a cutaway view of the bowl of FIG. 2A.

FIG. 2D is a cross-sectional view of a portion of the bowl of FIG. 2A.

FIG. 2E is a side view of the bowl of FIG. 2A.

FIG. 3A depicts a bowl of an aerosol device with nozzles that extend inward from a side wall of the bowl in an orientation that differs from that of FIG. 2A.

FIG. 3B is a top view of the bowl of FIG. 3A.

FIG. 4A depicts a bowl of an aerosol device having a single nozzle.

FIG. 4B is a top view of the bowl of FIG. 4A.

FIG. 5A depicts a bowl of an aerosol device having multiple nozzles.

FIG. 5B is a top view of the bowl of FIG. 5A.

FIG. 6A depicts a nozzle of an aerosol device.

FIG. 6B is a cross-sectional view of the nozzle head of FIG. 6A.

FIG. 7A depicts a liquid outlet having open rectangular slots and an open tip.

FIG. 7B depicts a liquid outlet having closed rectangular slots and a closed tip.

FIG. 7C depicts a liquid outlet having closed curved slots and an open tip.

FIG. 7D depicts a liquid outlet having closed angled slots and a closed tip.

FIG. 8A depicts a bowl of an aerosol device having a central post.

FIG. 8B is a first cutaway view of the bowl of FIG. 8A.

FIG. 8C is second cutaway view of the bowl of FIG. 8A.

FIG. 9A depicts a bowl of an aerosol device having a tapered central post.

FIG. 9B is a cutaway view of the bowl of FIG. 9A.

FIG. 10A depicts a bowl of an aerosol device having a lid with an aperture.

FIG. 10B is a cutaway view of the bowl of FIG. 10A having a lid with an aperture.

FIG. 10C is a cutaway view of a bowl having a lid similar to that in FIG. 10A with a larger aperture.

FIG. 11A depicts a bowl of an aerosol device having a lid with a post.

FIG. 11B is a first cutaway view of the bowl of FIG. 11A.

FIG. 11C is a second cutaway view of the bowl of FIG. 11A.

FIG. 12 depicts a flow diagram for an aerosol process.

FIG. 13 depicts a forced air sensor tube for an aerosol device.

FIG. 14 depicts an aerosol device in a room.

FIG. 15 depicts a flow chart for a process for disinfecting a room.

FIG. 16 depicts a flow chart for a process for disinfecting a room.

FIG. 17 shows propagation over time of liquid droplets of various size ranges produced by an aerosol device.

FIG. 18 shows penetration of cloth samples with liquid droplets of various sizes produced by an aerosol device.

DETAILED DESCRIPTION

FIG. 1 depicts aerosol device 100. Aerosol device 100 forms an aerosol from a liquid and a gas. The aerosol includes droplets of the liquid suspended in the gas. A majority of the droplets are submicron droplets, having a maximum dimension less than 1 μm. In some implementations a majority of the droplets have a maximum dimension in a range between 0.1 μm and 0.7 μm or between 0.3 μm and 0.7 μm. As used herein, a "majority" of droplets refers to 50% or more of a total number of droplets. In some cases, a majority of droplets includes at least 60%, at least 70%, at least 80%, at least 90%, or at least 95% of a total number of droplets. The submicron droplets diffuse away from the aerosol device.

The liquid used to form the aerosol typically includes a substance to be dispersed, such as medicaments, pesticides, biocides, preservatives, fertilizers, perfumes, oils, nanoparticles, cleaning agents, rodenticides repellants, attractants, or disinfectants. In some implementations, the liquid is an aqueous composition. The submicron droplets also include the substance to be dispersed. In one example, an aerosol including submicron droplets that have an effective concentration of disinfectant may be used to kill microorganisms, such as bacteria, archaea, protozoa, algae, fungi, viruses, and multicellular animal parasites. The microorganisms may be present in the air, on a surface, or in a porous article contacted by the aerosol.

Suitable disinfectants include hypochlorous acid, quaternary ammonium compounds, and bleach. The hypochlorous acid may be formed by electrolysis of an aqueous solution of sodium chloride, calcium chloride, or potassium chloride. A concentration of disinfectant in a solution of hypochlorous acid may be understood as the concentration of free available chlorine (e.g., hypchlorous acid and hypochlorite ions) in the solution. A concentration of free available chlorine may be expressed as parts per million by weight (ppm). A concentration of disinfectant in an aerosol including droplets containing hypochlorous acid may be expressed in ppm of free available chlorine in the droplets. A concentration of free available chlorine of at least 1800 ppm in an aerosol with a maximum droplet dimension in a range between 0.1 μm and 0.7 μm or between 0.3 μm and 0.7 μm is effective to kill a variety of microorganisms upon exposure to the aerosol for a sufficient length of time. A length of time sufficient to kill microoganisms upon exposure to such an aerosol depends on factors including the type of microorganism(s), the infestation level of the microorganism(s), a concentration of the disinfectant in the droplets, a distance of the microorganism(s) from the aerosol device, and environmental variables such as relative humidity, temperature, and barometric pressure.

Referring again to FIG. 1A, components of aerosol device 100 are arranged in housing 102. Housing 102 includes bowl 104 with one or more nozzles 106 extending from side wall 108. Side wall 108 is typically cylindrical. Aerosol device 100 generates an aerosol in nozzles 106 by forming a suspension of liquid droplets in a gas, such as air. Bowl 104 includes rim 110. Aerosol device 100 includes user interface 112. In some implementations, aerosol device 100 may be operated remotely via a user interface on a device such as a personal computer or a personal digital assistant. In some implementations, aerosol device 100 includes handle 114 and wheels 116, which allow a user to maneuver the aerosol device. Aerosol device 100 typically includes a liquid compartment, accessible through cover 118. In some implementations, aerosol device 100 includes a battery and is powered by direct current. In some implementations, aerosol device 100 is powered by alternating current and includes a power cord for electrically coupling to a source of alternating current.

Figure 1B:
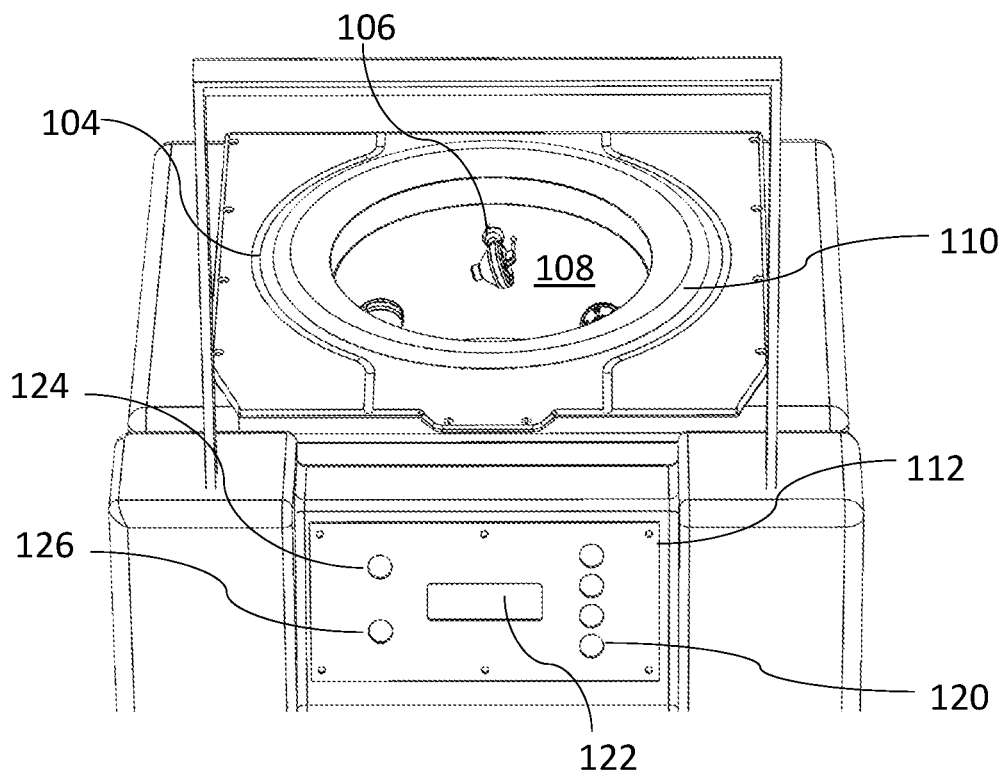

FIG. 1B is a close-up view of a portion of aerosol device 100, including bowl 104 and user interface 112. As depicted, bowl 104 includes four nozzles 106 that extend inward from side wall 108. Nozzles 106 are spaced evenly around an inner diameter of bowl 104. In some implementations, aerosol device 100 includes one, two, three, four, five, six, or more nozzles that extend inward from side wall 108. When aerosol device 100 includes multiple nozzles, the nozzles may form one or more rows around side wall 108. User interface 112 may include control features 120 including, for example, a power switch, a pause/resume switch, and a kill switch. In some implementations, user interface 112 includes a control feature to control or adjust a display on screen 122. User input may be provided to aerosol device 100 and displayed on screen 122 via one or more input control features 124, 126.

Figure 1C:
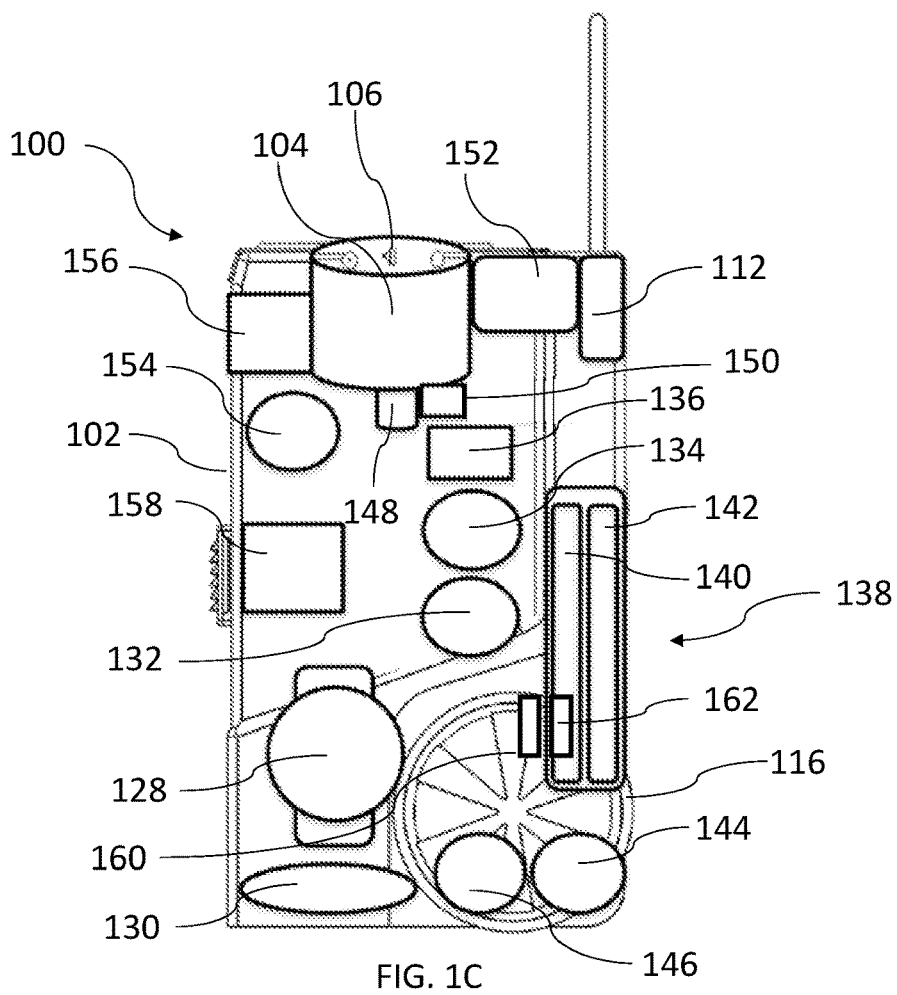

FIG. 1C depicts components of aerosol device 100 in housing 102. Air is provided to the one or more nozzles in bowl 104 by pressurized gas source 128. In some implementations, pressurized gas source 128 is an adjustable air compressor pump. More than one air compressor may be used to provide compressed air to nozzles 106 in bowl 104. Air from the ambient environment is filtered and compressed by pressurized gas source 128. In some implementations, pressurized gas source 128 may be external to aerosol device 100. Cooling fan 130 may cool the air compressor pump(s) as appropriate. Air pressure or flow rate to the one or more nozzles 106 in bowl 104 may be regulated by air pressure (or air flow) regulator 132. If pressurized gas source 128 is sized to match the air demand of nozzles 106 or a pressure or flow of the pressurized gas source is controlled by adjusting a motor speed of the air compressor pump electronically, the air pressure (or air flow) regulator may not be needed. From regulator 132, the air may be provided to air accumulator 134 to smooth out the air flow pulsing caused by certain types of pressurized gas sources. Air accumulator 134 may include a flexible conduit, such as silicone tubing. The flexible conduit may filter out air pulsing of pressurized gas source 128. The air is then sent to gas manifold 136 to provide a portion of the air to each nozzle 106 in bowl 104. Gas manifold 136 is selected based at least in part on the number of nozzles 106 to be supplied with air. The air enters each nozzle 106 through a compressed air tube and then into a chamber in each nozzle, where the air is exits the chamber at a high speed, past a liquid outlet in a conduit that provides liquid from liquid compartment 138 to the chamber. This air flow over the liquid outlet shears off liquid droplets, creating an aerosol.

Liquid compartment 138 is removably attached to aerosol device 100 and includes a liquid container 140 that supplies the aerosol device with the liquid to be aerosolized. Liquid container 140 may contain a disinfectant in the form of an aqueous composition. In some implementations, liquid compartment 138 also includes waste container 142 that provides a containment mechanism for waste generated by aerosol device 100. In some implementations, each of liquid container 140 and waste container 142 is coupled to housing 102 via a sealing connector. Each sealing connector inhibits the flow of liquid through the sealing connector when the connector is disconnected, such as when liquid compartment 138 is removed from aerosol device 100. In some implementations, liquid compartment 138 is fixed in aerosol device 100, such that sealing connectors are not necessary. Two one-way valves may be located in disinfectant reservoir rather than housing 102, in combination with a single sealing connector.

Liquid container 140 and waste container 142 may be flexible bags, bottles, or rigid containers. In some implementations, liquid compartment 138 is a bag-in-box container that keeps liquid in disinfectant reservoir 140 and waste container 142 protected from light and oxygen to inhibit chemical degradation of the liquids. The outer box may be plastic or cardboard and corrugated for added strength. When liquid container 140 or waste container 142 is a rigid material, a suitable vent on the container is provided to inhibit a suction as fluid is removed from the container Aerosol device 100 includes a liquid recirculation path and a reservoir fill/drain path. The reservoir fill/drain path includes reversible pump 144 that has a forward mode and a reverse mode. In the forward mode, fluid from liquid container 140 is pulled by reversible pump 144 through a sealing connector followed by a one-way valve. The one-way valve allows fluid to travel in a single direction from liquid container 140. From the one-way valve, the fluid from liquid container 140 is then analyzed by one or more liquid sensors 146 to determine if the fluid has been tampered with or is not within required specifications. These sensors may include a pH sensor, an oxidation-reduction potential (ORP) sensor, an electrical conductivity (EC) sensor, a free available chlorine (FAC) sensor, a total available chlorine (TAC) sensor, a temperature sensor, or any combination thereof. If the fluid is determined to be acceptable, the fluid then advances under pressure from reversible pump 144 to reservoir 148 of bowl 104. If the fluid is not acceptable, the operation is stopped and appropriate action is taken. Reservoir fluid level sensor 150 provides a full signal to processor 152 to turn off reversible pump 144 when the reservoir is full. As fluid is drawn from reservoir 148 into nozzles 106, the reservoir is drained and reservoir fluid level sensor 150 provides a fluid low signal to processor 152. Processor 152 uses this input to determine if reversible pump 144 should be turned on.

In the reverse mode of reversible pump 144, fluid is pulled from reservoir 148 by the reversible pump operating in reverse through the sensors as described herein, through the one-way valve and into waste container 142. A configuration of the one-way valves allows the fluid returning to liquid compartment 138 to enter waste container 142. The reverse mode is used to determine if improper or out of date disinfectant has been added to bowl 104 by a user, by running the fluid from the reservoir past liquid sensors 146. Waste may include fluid left in bowl 104 from the last use, fluid added to the bowl by the user that is not approved for use, and the like.

The liquid recirculation path is the path the source liquid takes from reservoir 148 to nozzles 106. Recirculation pump 154 is connected between reservoir 148 and liquid manifold 156. Liquid manifold 156 typically has an outlet for each nozzle 106. A nozzle tube of each nozzle 106 is connected to liquid manifold 156 via a conduit. Recirculation pump 154 pulls liquid from reservoir 148 and pushes it into liquid manifold 156 where it is divided and sent to nozzles 106 through nozzle tubes and then through a fluid outlet at the tip of each nozzle. Recirculation pump 154 may be an adjustable speed recirculation pump that allows processor control of liquid flow rates.

In some implementations, reservoir 148 is fluidly coupled to the nozzle tube of each nozzle 106 via a conduit. As air passes the fluid outlet of each nozzle 106, a suction is created on a tip of each nozzle that pulls fluid from reservoir 148. Due to the shearing action of the air over the fluid outlet in each nozzle tip, droplets are sheared from fluid outlet and into the air as the air leaves nozzle 106. Large droplets then impact side wall 108 of bowl 104 and return to reservoir 148 while small droplets exit the bowl.

In some implementations, aerosol device 100 includes one or more air sensors 158 coupled to processor 152. Air sensors 158 may include, for example, a temperature sensor, a relative humidity sensor, a barometric pressure sensor, or a combination thereof. Processor 152 may be operatively coupled to both recirculation pump 154 and pressurized gas source 128 and configured to monitor ambient temperature, pressure, and relative humidity of a target volume, and to control both the pump and the pressurized gas source to provide an aerosol to the target volume for a length of time sufficient to achieve a selected concentration of a disinfectant in the target volume.

In some implementations, aerosol device 100 includes RFID sensor 160 coupled to processor 152, and liquid compartment 138 or liquid container 140 includes RFID tag 162. This arrangement allows aerosol device 100 to identify liquid compartment 138 or liquid container 140 and its contents and to read and write information to the RFID tag. RFID information may include, for example, disinfectant fill level, waste fill level, disinfectant expiration date, liquid type, liquid strength, disinfectant FAC, disinfectant Ph, aerosol device configuration specific to the liquid, dates for each use and amounts used, error codes generated by the device, or a combination thereof. RFID tag 162 may also be read by a manufacturer of the disinfectant for similar reasons.

FIGS. 2A-2E depict bowl 104 of aerosol device 100. FIG. 2A depicts bowl 104 with nozzles 106 that extend from side wall 108. Bowl 104 includes rim 110 and reservoir 148. In some implementations, bowl 104 includes lip 200 that extends inward (e.g., 0.5 cm to 3 cm) from side wall 108 of bowl 104. Each nozzle 106 defines outlet orifice 202 and extends from side wall 108 via stem 204. Fluid is provided to each nozzle 106 via nozzle tube 206.

FIG. 2B depicts bowl 104 with nozzles 106, rim 110, bottom 208, and drain 210, through which liquid in the bowl drains to the reservoir. In some implementations, drain 210 is covered by screen 212. Bottom 208 and side wall 108 together define an interior surface of bowl 104 bounding a bowl volume. In some implementations, as depicted in FIG. 2B, stem 204 extends perpendicularly from side wall 108.

FIG. 2C is a cutaway view of bowl 104 with nozzles 106, side wall 108, rim 110, reservoir 148, bottom 208, and lip 200. Rim 110 may serve as a mount for mounting the bowl to aerosol device 100. Rim 110 is slightly tilted toward the bowl opening to help capture moisture that attaches or condenses on the rim. In some implementations, as depicted in FIG. 2C, bottom 208 of bowl 104 is sloped to allow fluid that has been filtered out to quickly return to reservoir 148 for reuse.

FIG. 2D is a close-up view of a cross section of bowl 104 and shows a cross section of lip 200. Lip 200 extends inwardly from side wall 108 of bowl 104 to overhang the side wall about the bowl, with nozzles 106 disposed between the lip and a bottom of the bowl. At least a portion of the nozzle extends radially inward past the lip, and the lip defines a bowl outlet opening through which aerosol generated within the bowl passes out of the bowl.

FIG. 2E is a side view of bowl 104, and depicts gas manifold 136. Gas from gas manifold 136 is provided to nozzles 106 via a conduit that extends into bowl 104 through the side wall of the bowl. Liquid from liquid manifold 156 is provided to nozzles 106 via a conduit that extends into bowl 104 through a side wall of the bowl. Support ribs 214 help support and strengthen bowl 104 when the bowl is mounted to aerosol device 100 by rim 110.

Bowl 104 provides a staged filter system. Each stage successively filters the droplet size down further. The droplets are produced in the nozzle itself. The nozzle creates a high volume, coarse distribution of droplets. A first filtering stage is the side wall of the bowl. The high-volume spray from the nozzle obliquely contacts the side wall. Only the smaller droplets, those that can move with the air flow, avoid hitting the bowl wall by remaining in the air flow. The larger droplets impact the bowl wall and flow down to the reservoir via the drain. This fluid is then reused. A second filtering stage uses centrifugal force to separate the larger droplets. The air flow from the nozzle(s) creates a vortex within the bowl. Larger droplets are forced to the side wall as they flow within the vortex. The larger droplets that impact the bowl wall flow down to the reservoir via the drain for reuse. A third filtering stage includes lip 200 that extends inwardly from the side wall of the bowl. As the spiraling air flow approaches the lip, only small droplets make it past the lip due to the sharp change in radius. The underside of the lip toward the center of the bowl is curved downward to help keep air flow (and larger droplets) inside the bowl. The downward curve also encourages the larger drops that form on the lip to fall into the bowl instead of being blown out of the bowl.

Figure 2A:
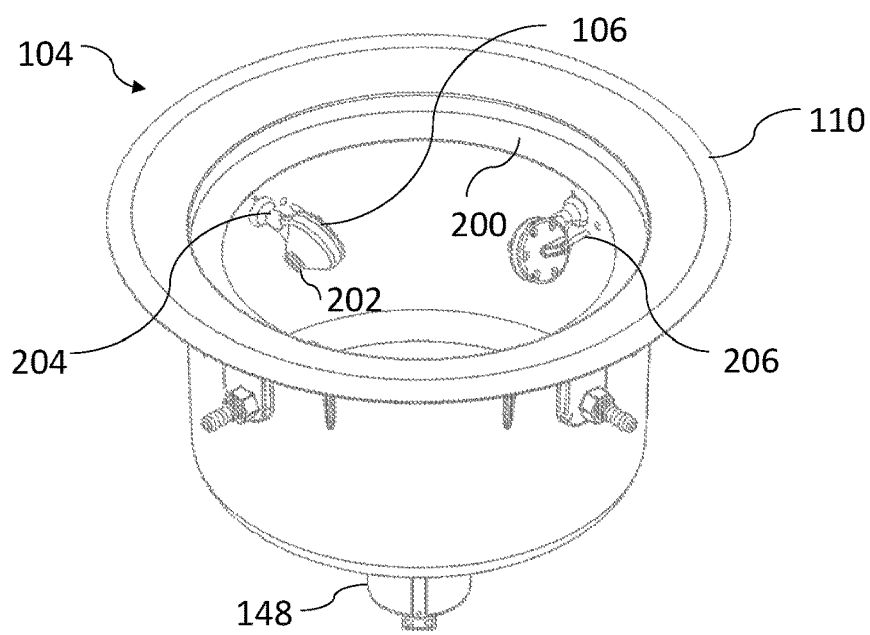
Figure 2B:
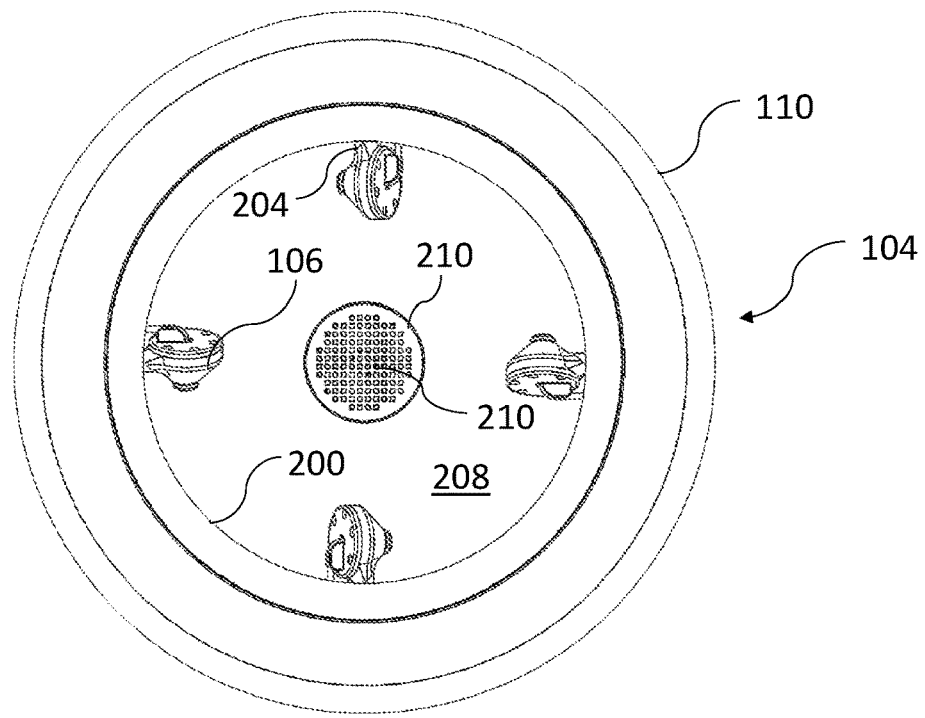
Figure 2C:
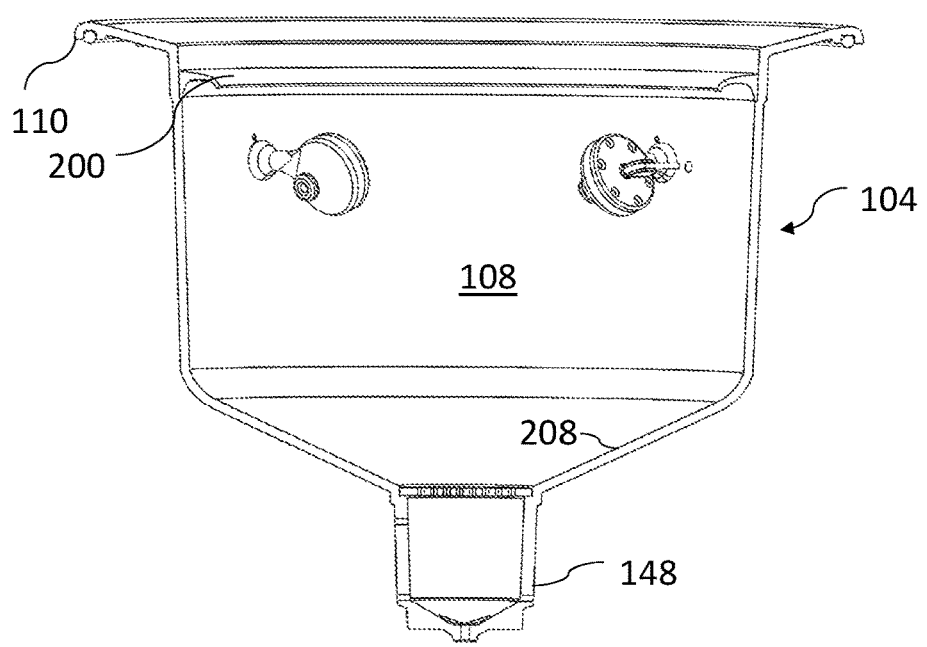
Figure 2D:
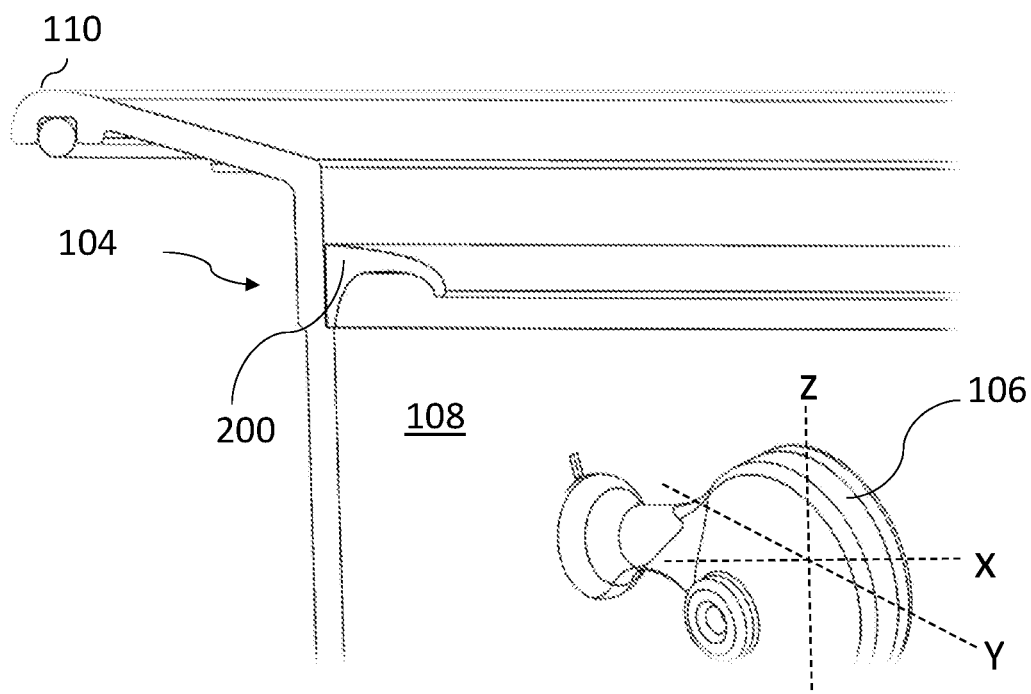
Figure 2E:
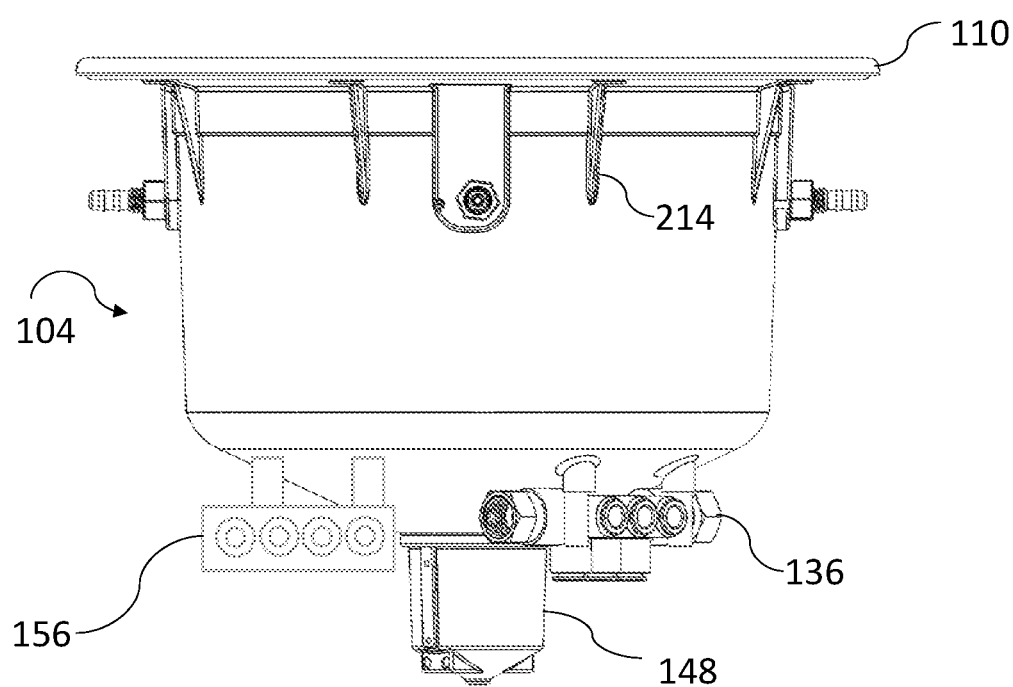

Nozzles 106 are positioned within bowl 104 to support the filtering stages. An orientation of nozzles 106 may be adjusted in at least six dimensions, including translation along and rotation about axes X, Y, and Z depicted in FIG. 2D. Translation of nozzle along axes X and Y affects how close the nozzle spray is toward the inside of the bowl. Both X and Y also affect, to a smaller degree, the angle of the nozzle spray to the bowl. The angle of the nozzle spray to the bowl is primarily affected by rotation about Z. A smaller Y value brings the nozzle close to the side of the bowl. The position may be optimized for a nozzle air pressure and liquid flow rate to maximize droplet generation of the desired droplet size. If the nozzle spray is too far from the bowl wall, the reduced spray velocity reduces a filtering capability of the bowl. If the nozzle spray is too close, none (or few) of the droplets will be able to avoid collisions with the wall or other droplets (since other droplets are very close when first leaving the nozzle output).

A position of nozzle 106 is typically adjusted along the Z axis and about the Y axis together. The rotary positioning about the Y axis directs the nozzle spray pattern down into or up out of the bowl. Translation along the Z axis lowers the nozzle down into or up out of the bowl. If the spray pattern is too high in the bowl (either from rotation about the Y axis facing the nozzle up or the Z axis axis translation being too high in the bowl), the spray pattern directly leaves the bowl without (or with minimal) filtering. If rotation about the Y axis faces the nozzle too far downward, too little of the spray pattern is directed toward rotating the gas within the bowl and the centrifugal filtering is reduced.

Nozzle rotation about the Z axis rotates the nozzle toward or away from the side wall along a horizontal axis of the bowl. If nozzle rotation about the Z axis directs the nozzle directly toward at the side wall, aerosol rotation within the bowl may be inhibited, such that filtering is insufficient. A Z axis rotational angle of 25° to 35° degrees toward a surface of the bowl (from perpendicular to a side wall of the bowl) facilitates production of small droplets from the aerosol device without significantly reducing filtering within the bowl. In some implementations, a Z axis rotation angle is about 30°. A distance of the nozzle output from the side wall may remain constant.

Screen 212 prevents objects from falling into reservoir 148 and possibly creating a plug hazard for tubing, pumps, and nozzle tubes. Reservoir 148 and screen 212 prevent splashing of the liquid collected at the bottom of the bowl due to aerosol movement within the bowl. A level of fluid in the reservoir may be detected with an optical sensor or a float-based sensor, or may be detected via ultrasonic methods, electrical conductivity, or other appropriate methods. The reservoir fluid level sensor data is read by the processor.

In some implementations, bowl 104 is used separately from housing 102 of aerosol device 100. In some implementations, bowl 104 is coupled to aerosol device 100 via an umbilical cord to allow placing of the bowl near vents or in attics, crawl spaces, and other harder to reach treatment areas. The umbilical cord may include a pressurized gas source or a conduit for a pressurized gas, disinfectant lines, and sensor and other electrical wiring. Bowl 104 may not require a reservoir if the fluid is pumped directly to the nozzles from a fluid container. In some implementations, bowl 104 may be replaceably removed from aerosol device 100.

One or more nozzles 106 may be mounted in a row along the upper part of side wall 108 of bowl 104. In some implementations, a spacing of the nozzles can be symmetric with equal spacing. The nozzles can be in more than one row along the inside of the bowl. In one examples, twelve nozzles are equally spaced apart in two rows of six, the rows being staggered with respect to each other. As depicted, bowl 104 includes four equally spaced nozzles 106.

In some implementations, nozzles 106 are mounted from a center support structure within bowl 104. Mounting the nozzles on side wall 108 of the bowl has the advantage of eliminating the loss of aerosol droplets from collision with the center support structure, as well as eliminating the loss of rotational energy of the air in the bowl from collision with the center support structure. The side mounted nozzles also reduce damage to components from items dropped into bowl and user jewelry such as necklaces getting caught on the center structure. The side mounted nozzles also simplify manufacturing and facilitate nozzle alignment.

Bowl 104 advantageously increases a concentration of smaller droplets in the aerosol. In some implementations, bowl 104 includes an increased number of smaller nozzles. The shear force across fluid outlet increases with air flow speed across the outlet. The smaller chamber of a smaller nozzle provides a higher lateral air flow speed and therefore a higher shear force at the same pressure and lower air flow, thereby decreasing droplet size and increasing the number of droplets per unit of air flow and resulting in a reduction in required air flow. In addition, smaller nozzles result in closer spacing between nozzles and therefore more room for additional nozzles or rows of nozzles within the same bowl size. Droplet generation at reduced air flow allows for smaller power sources or an increase in the total number of nozzles for the same power.

Figure 3A:
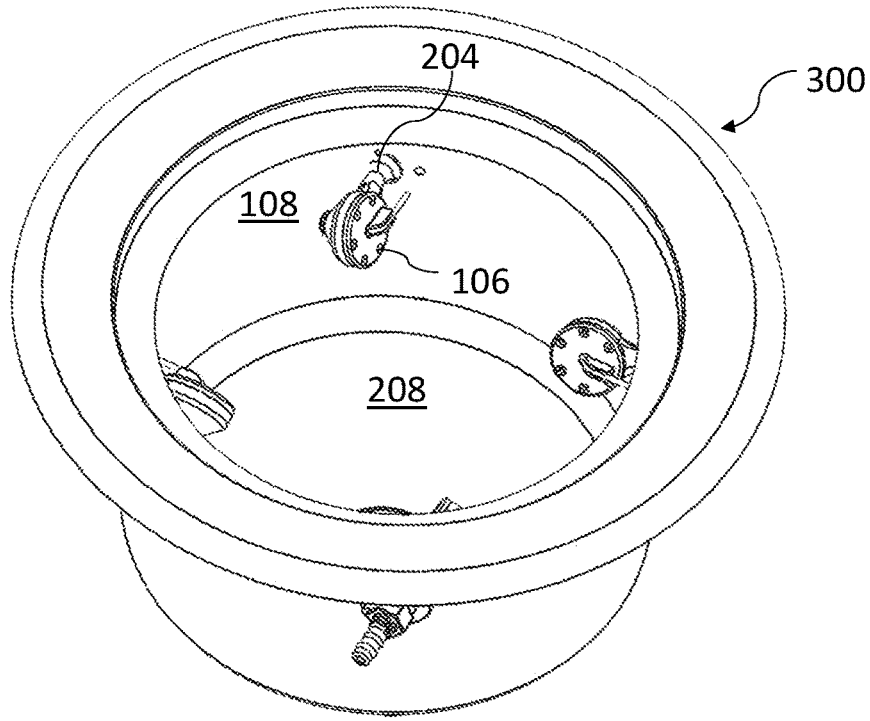
Figure 3B:
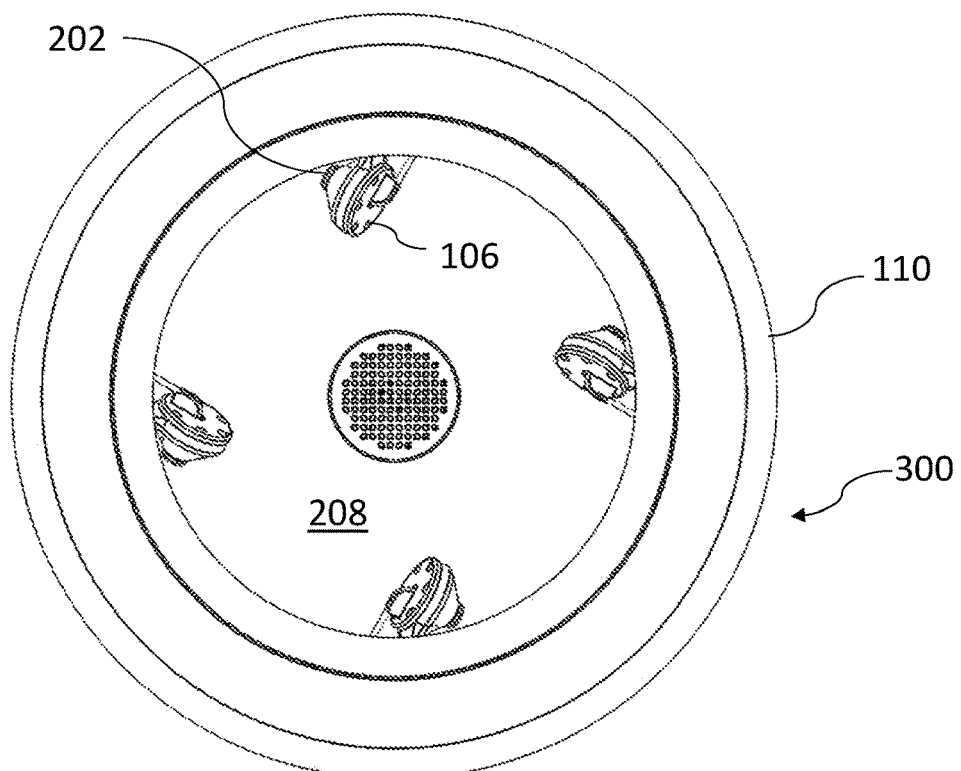

FIG. 3A depicts bowl 300 with nozzles 106 having an orientation rotated inward toward a side wall of the bowl by rotating about the Z axis a range of angles of 25° to 35°, or about 30°, such that stem 204 of the nozzle forms an angle of about 30° with respect to a line that extends perpendicularly from side wall 108 through a center of the stem at the side wall. FIG. 3B is a top view of bowl 300. As depicted in FIGS. 3A and 3B, outlet orifice 202 of nozzle 106 is directed, projected in a plane perpendicular to the primary longitudinal axis of the bowl, along a chord of a circle defined by side wall 108, such that a distance between the outlet orifice and the side wall, along the chord and in a spray direction of the nozzle, is less than ⅓ an overall length of the chord.

Figure 4A:
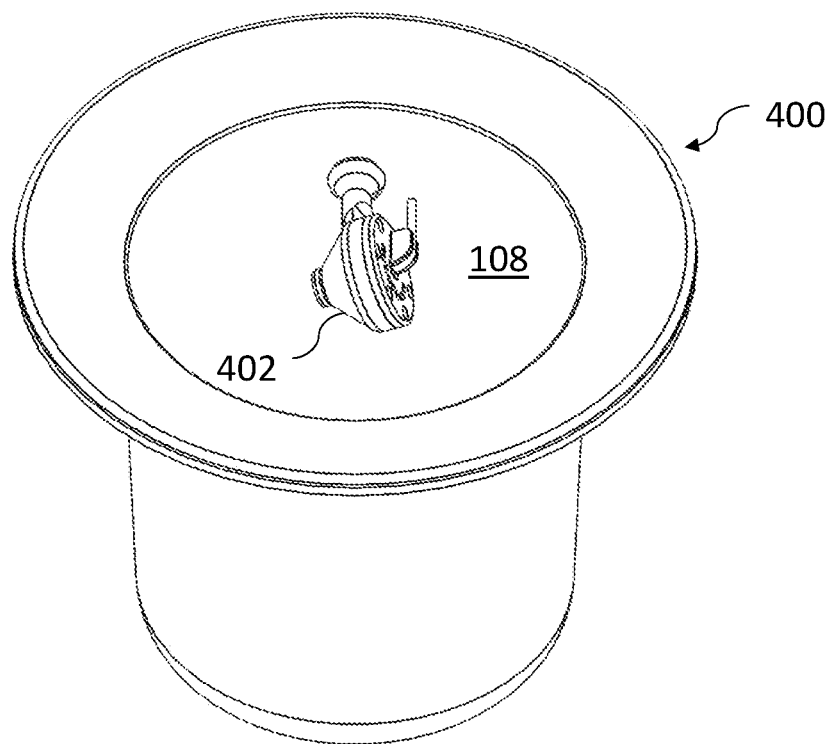
Figure 4B:
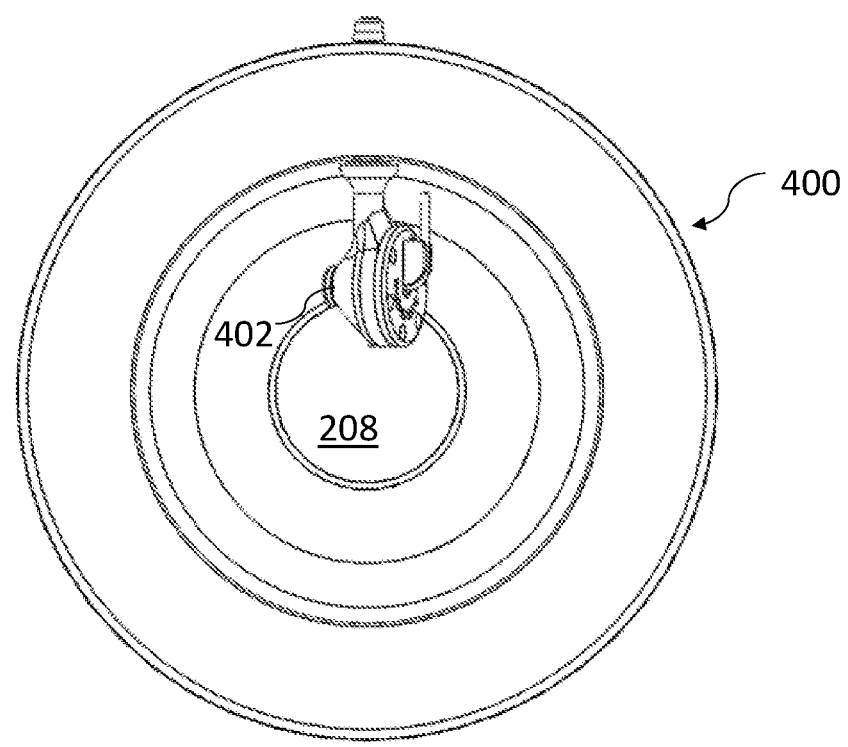

FIG. 4A depicts bowl 400 with a single nozzle 402. FIG. 4B is a top view of bowl 400. Bowl 400 and nozzle 402 may be similar to bowl 104 and nozzle 106 in structure and function, but smaller in size. A single nozzle may be operable with a smaller compressor that can be run on battery power, which may be advantageous for applications requiring portability such as treating small hotel rooms and walk through disinfection stations. Decreasing an internal diameter of the bowl increases the rotational speed of the aerosol within the bowl. This improves the efficiency of the second and third filtering stages as they are both based on centrifugal forces, but limits the number of nozzles that can be used and tightens their spacing. In some implementations, bowl 400 includes two or three nozzles.

Figure 5A:
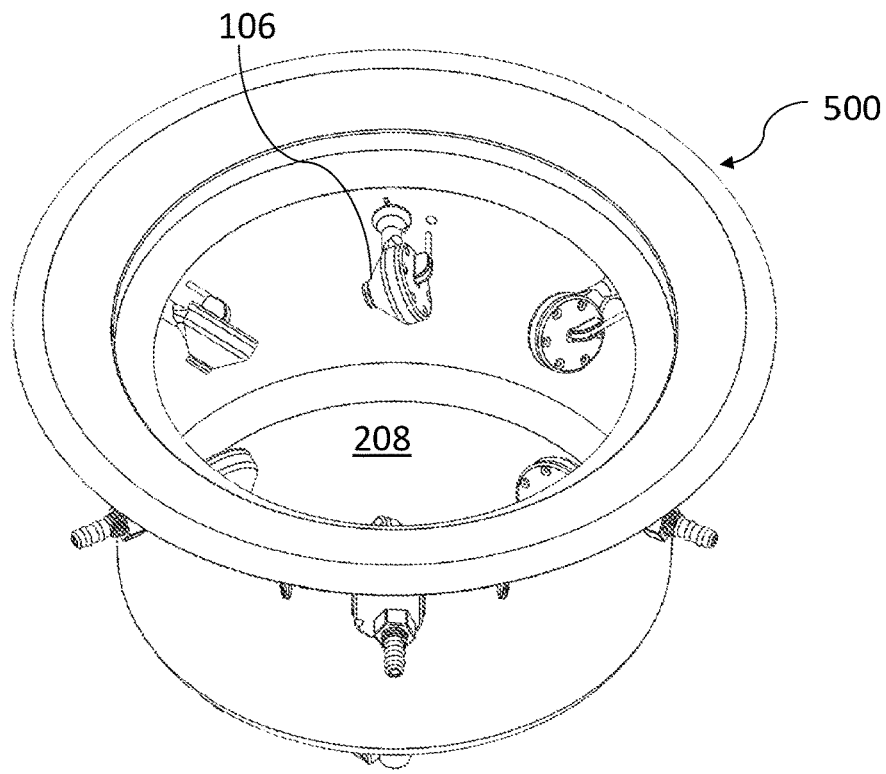
Figure 5B:
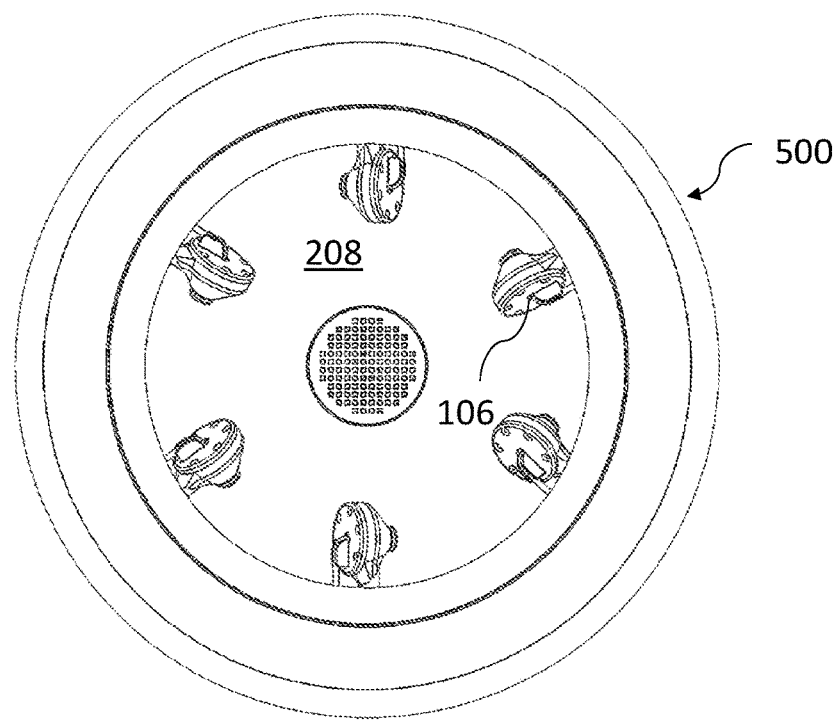

FIG. 5A depicts bowl 500 with six nozzles 106. Nozzles 106 may be equally spaced about side wall 108 of bowl 500. FIG. 5B is a top view of bowl 500.

Figure 6A:
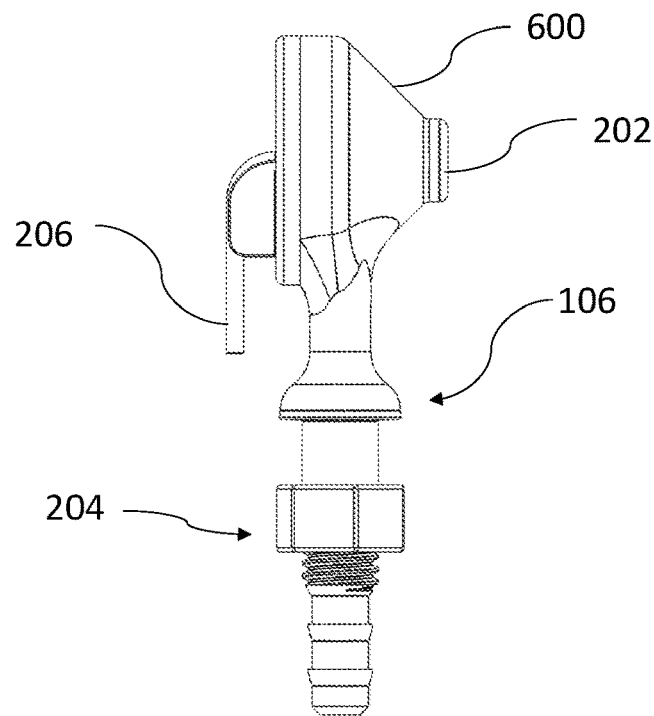

FIG. 6A depicts nozzle 106. Nozzles suitable for aerosol devices described herein include vortical nozzles, internal air mix nozzles, external air mix nozzles, siphon fed nozzles, and other air atomizing nozzles that provide the submicron drop distribution described herein. An example of a suitable internal mix nozzle is Pressure-fed Internal Mix Narrow Angle (XAPR) nozzle available from BETE Fog Nozzle, Inc. In an internal mix nozzle, liquid and air are injected into a mixing chamber inside the nozzle under pressure and expelled out together. Nozzle 106 includes nozzle head 600, outlet orifice 202, stem 204, and nozzle tube 206. Nozzle 106 is typically coupled to a side wall of a bowl via stem 204.

Figure 6B:
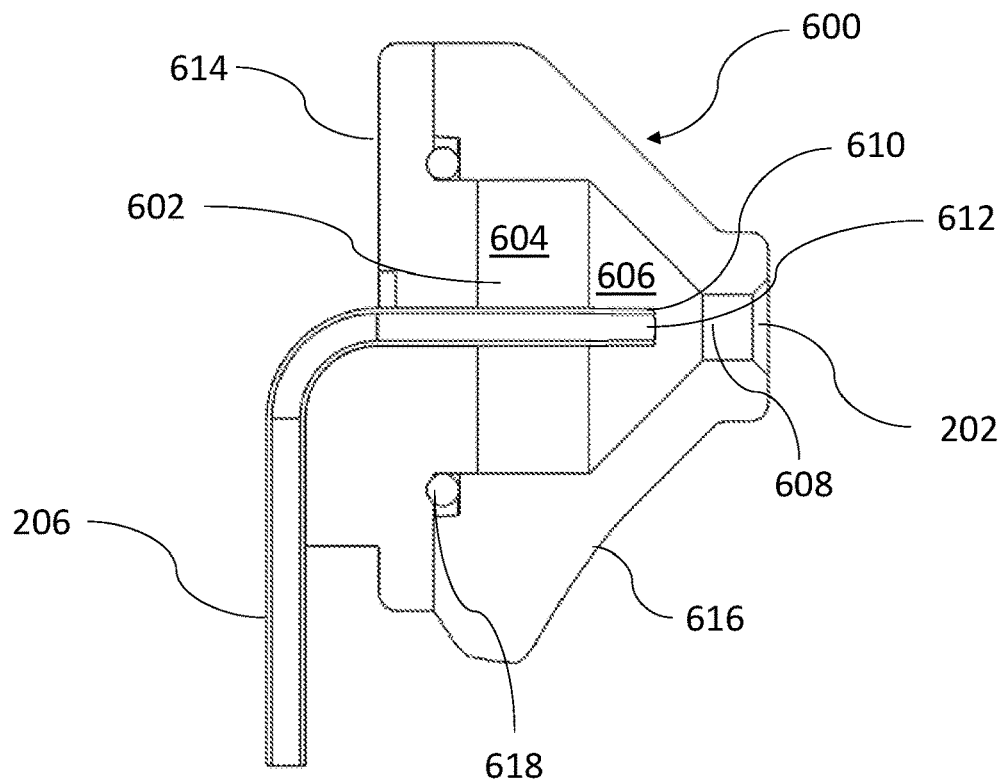

FIG. 6B is a cutaway view of nozzle head 600, showing chamber 602. As depicted, chamber 602 is a vortical chamber including first cylindrical portion 604, frustoconical portion 606, and second cylindrical portion 608. Nozzle tube 206 is positioned in chamber 602. In some implementations, tip 610 of nozzle tube 206 defines liquid outlet 612 and is positioned in second cylindrical portion 606 of chamber 602. In some implementations, nozzle head 600 includes nozzle back plate 614 removably coupled to nozzle housing 616. Gasket 618 forms a seal between nozzle back plate 614 and nozzle housing 616. In some implementations, nozzle back plate 614 and nozzle housing 616 are lockingly engaged by, for example, a twist lock mechanism. In some implementations, nozzle tube 206 is machined or molded as part of nozzle back plate 614 to simplify manufacturing, assembly, and adjustments.

Pressurized gas enters first cylindrical portion 604 of chamber 602 at an offset, and the offset air spins within the first cylindrical portion. The air is then forced by the incoming pressurized gas into frustoconical portion 606. As the cone diameter reduces, the air is forced to spin faster. This rotating air passes over liquid outlet 612 in tip 610, generating a high shear force, shearing off tiny droplets of liquid into the airstream, creating an aerosol. The aerosol then exits nozzle 106 through outlet orifice 202.

Liquid outlet 612 of tip 610 may have a variety of configurations. In some implementations, liquid outlet 612 includes slotted openings or elongated slots communicating from inside nozzle tube 206 to outside the nozzle tube, the slots each having a width defined between two surfaces of the nozzle tube. The two surfaces of nozzle tube 206 may be parallel, such that the width of each slot is constant. In some implementations, the width of each slot varies over a length of the slot by a maximum value (e.g., 10%). At least one end of each slot may be formed by two square or angled corners, or formed by a radius. The slots may be open or closed at tip 610 of liquid outlet 612. Tip 610 may be open or closed. Liquid outlet 612 of tip 610 may include one or more slots (e.g., two, three, four, five, or six slots). In some implementations, each slot defines a longitudinal axis parallel to a longitudinal axis of nozzle tube 206 proximate tip 610. In some implementations, each slot defines a longitudinal axis parallel forming an acute angle with a longitudinal axis of nozzle tube 206 proximate tip 610.

Figure 7A:
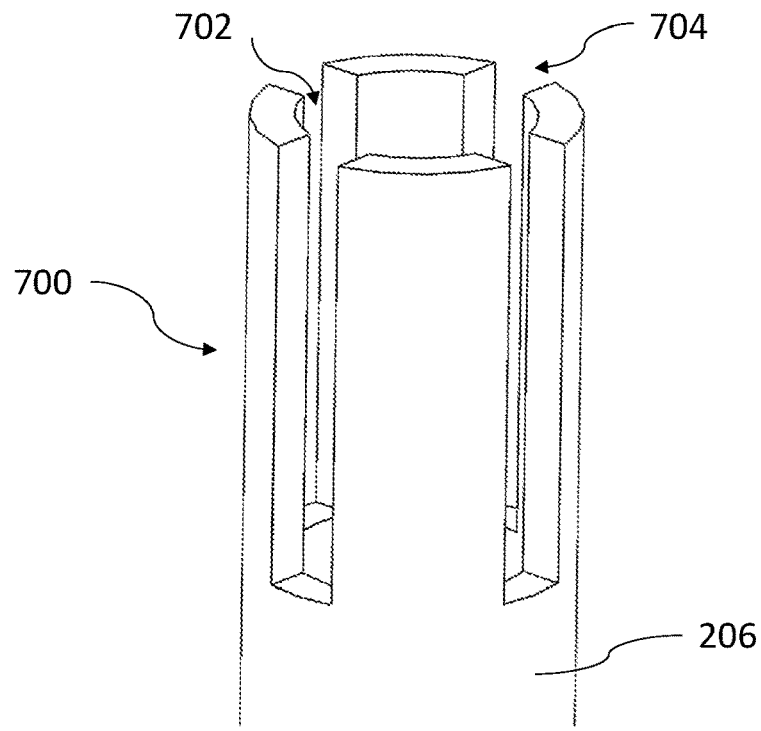

FIG. 7A depicts liquid outlet 700 of nozzle tube 206. Liquid outlet 700 defines elongated slots 702. Each slot 702 is open at one end and has one end formed by two square corners. In some implementations, each slot 702 has one end formed by a radius. Each slot 702 defines a longitudinal axis parallel to a longitudinal axis of tube 206 proximate tip 704. Tip 704 of liquid outlet 700 is open.

Figure 7B:
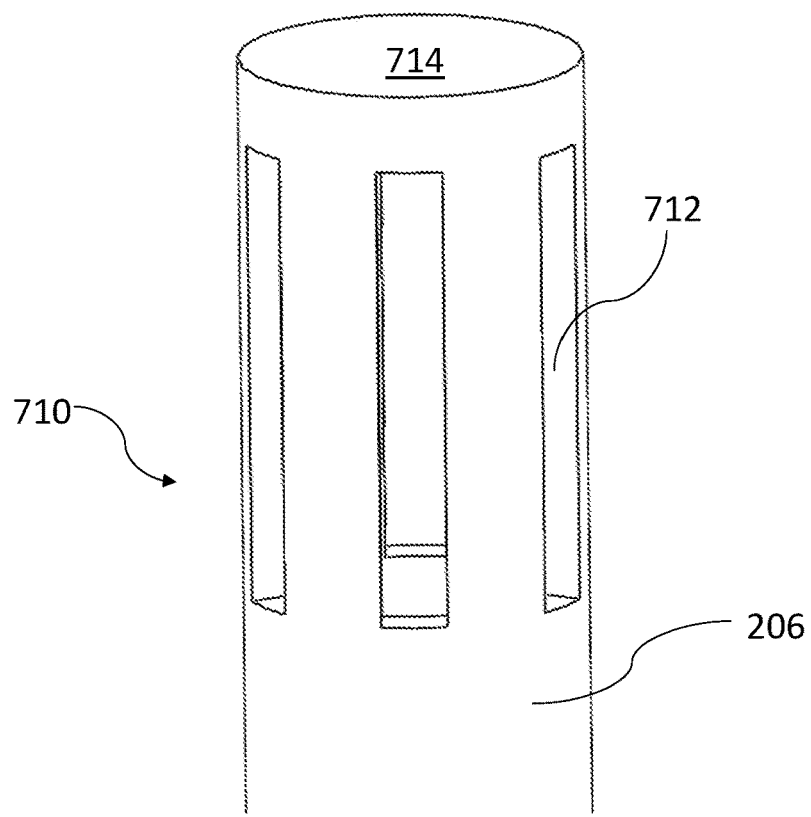

FIG. 7B depicts liquid outlet 710 of nozzle tube 206. Liquid outlet 710 defines elongated slots 712. Each slot 712 is closed at both ends, and both ends are formed by two square corners. Each slot 712 defines longitudinal axis parallel to a longitudinal axis of nozzle tube 206 proximate tip 714. Tip 714 is closed.

Figure 7C:
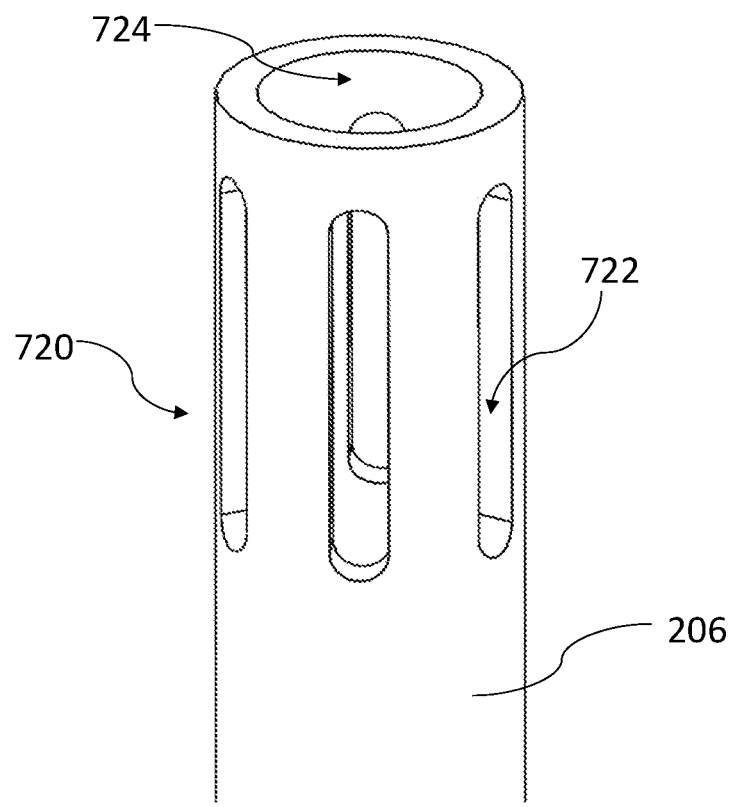

FIG. 7C depicts liquid outlet 720 of nozzle tube 206. Liquid outlet 720 defines elongated slots 722. Each slot 722 is closed at both ends, and both ends are formed by a radius. Slots with ends formed by a radius may reduce turbulence of the liquid flow. Each slot 722 defines a longitudinal axis parallel to a longitudinal axis of nozzle tube 206 proximate a tip. As depicted, tip 724 is open. In some implementations, tip 724 is closed.

Figure 7D:
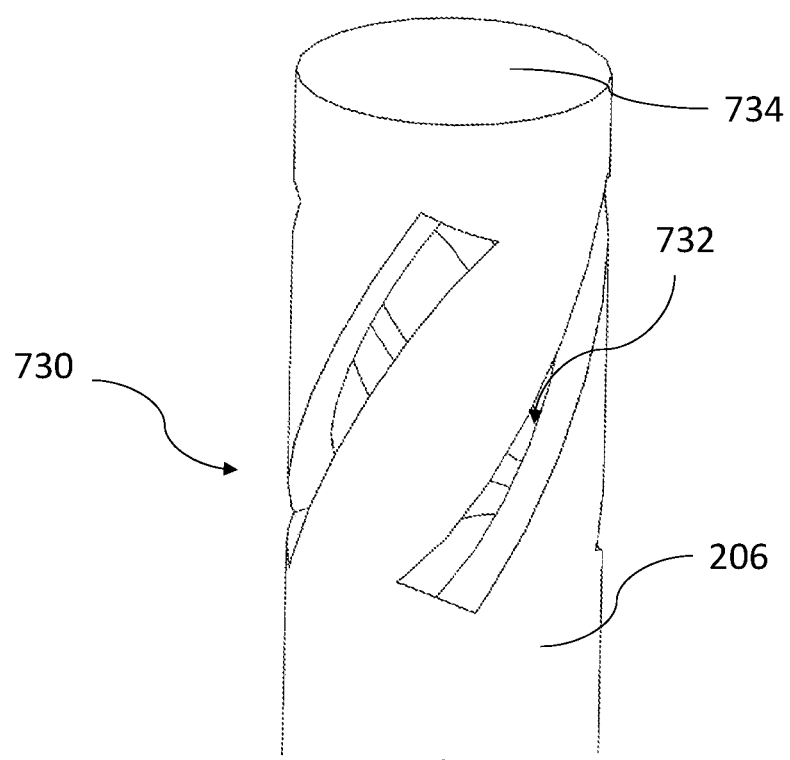

FIG. 7D depicts liquid outlet 730 of nozzle tube 206. Liquid outlet 730 defines elongated slots 732. Each slot 732 is closed at both ends, and both ends are formed by angled corners. In some implementations, both ends may be formed by a radius. A center line along the length of each slot 732 is perpendicular to spiral air flow as it passes the slot. As depicted, tip 734 is closed. Air flow perpendicular to the slot provides high shear force and efficient generation of small droplets. In some implementations, tip 734 is open.

Figure 8A:
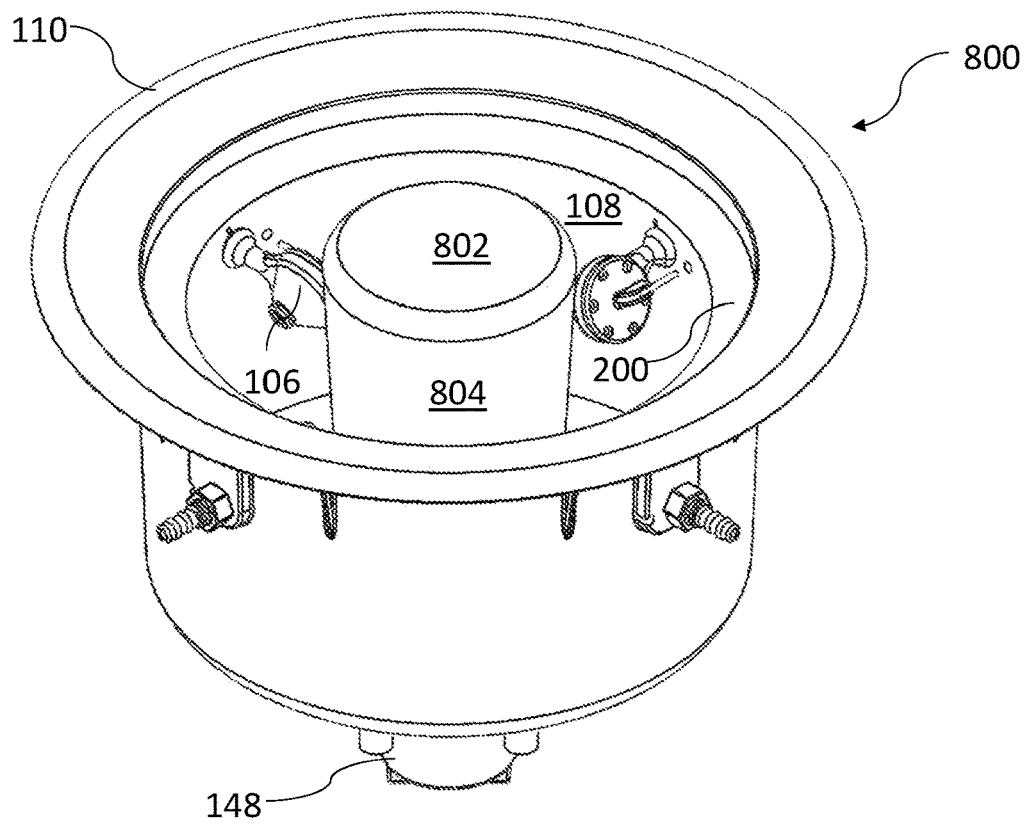
Figure 8B:
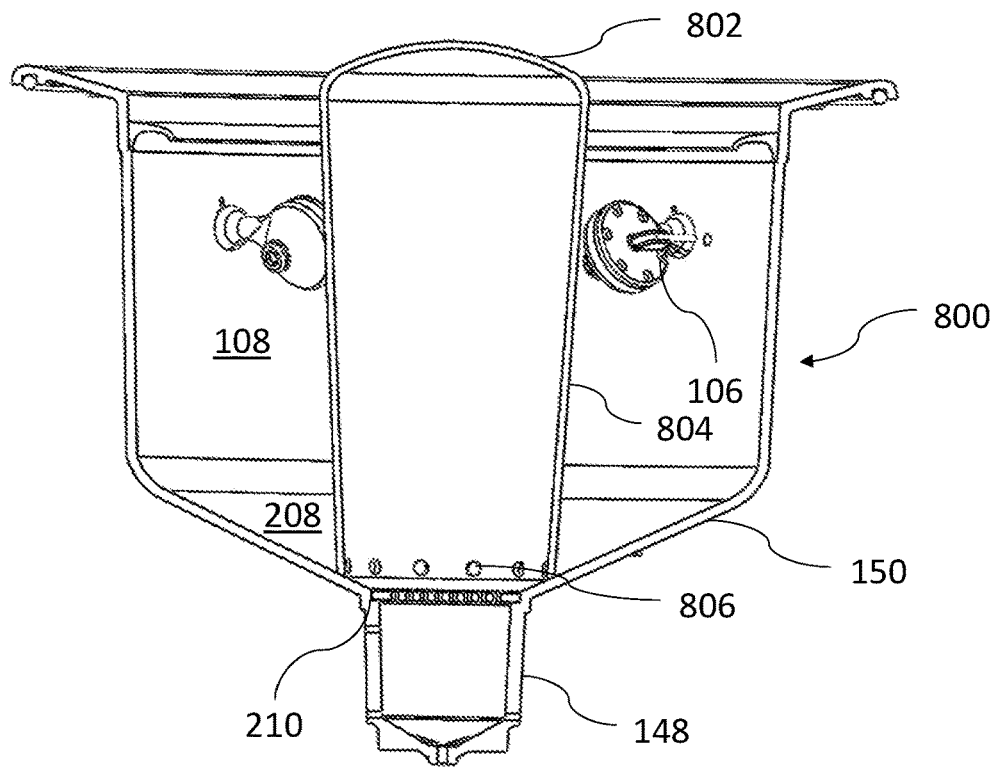
Figure 8C:
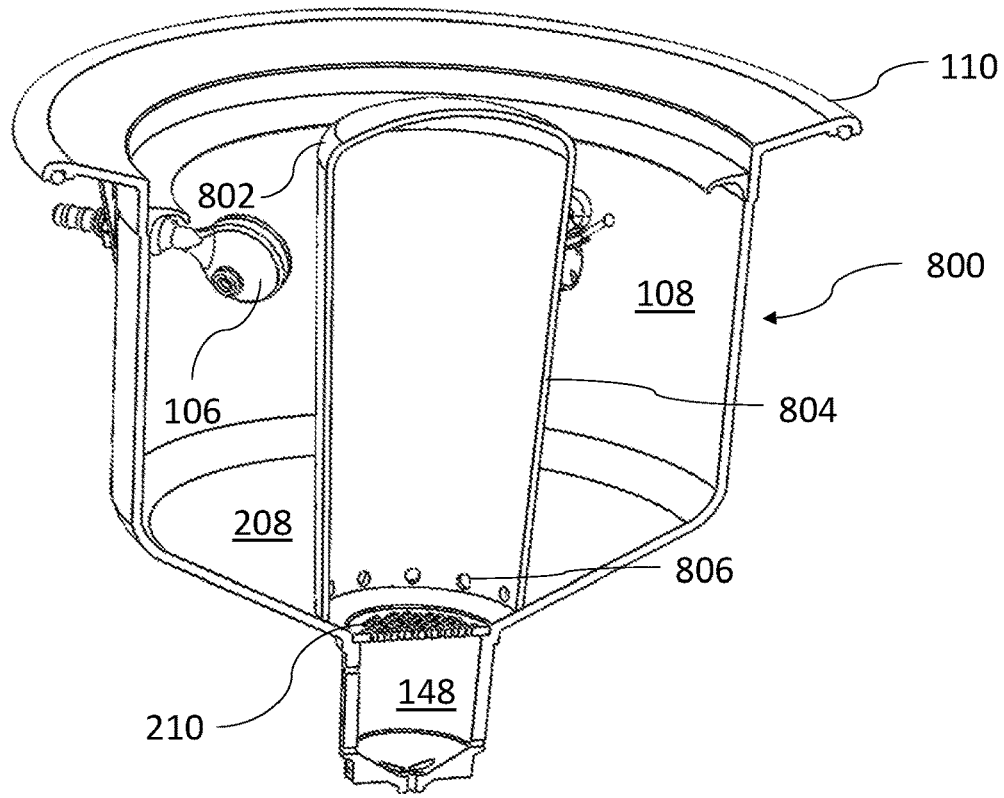
Figure 9A:
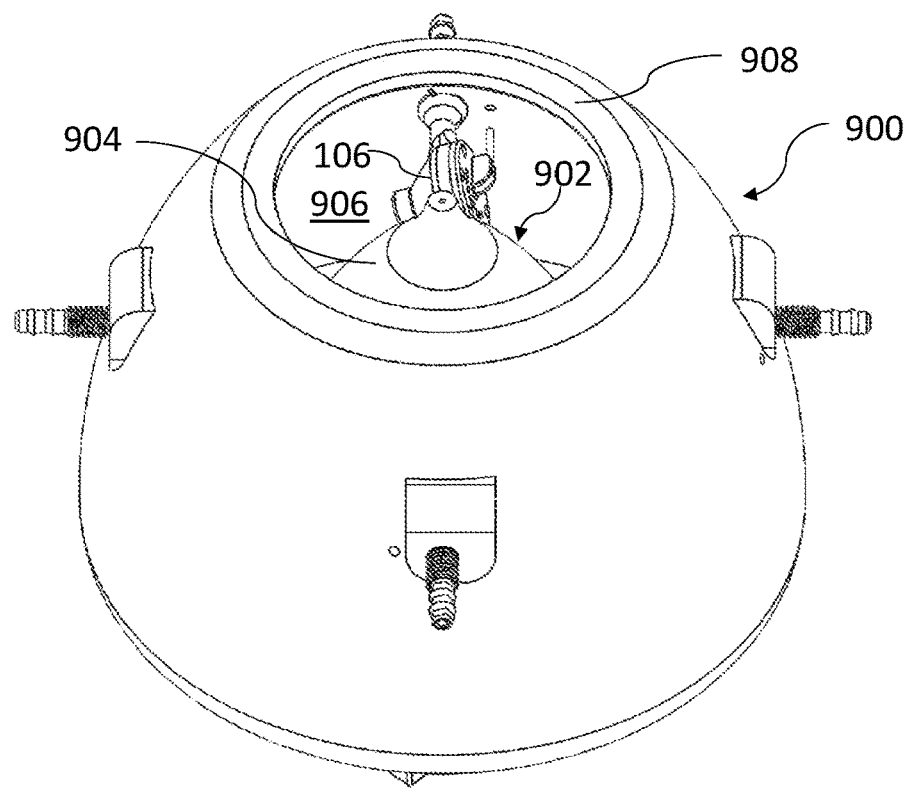
Figure 9B:
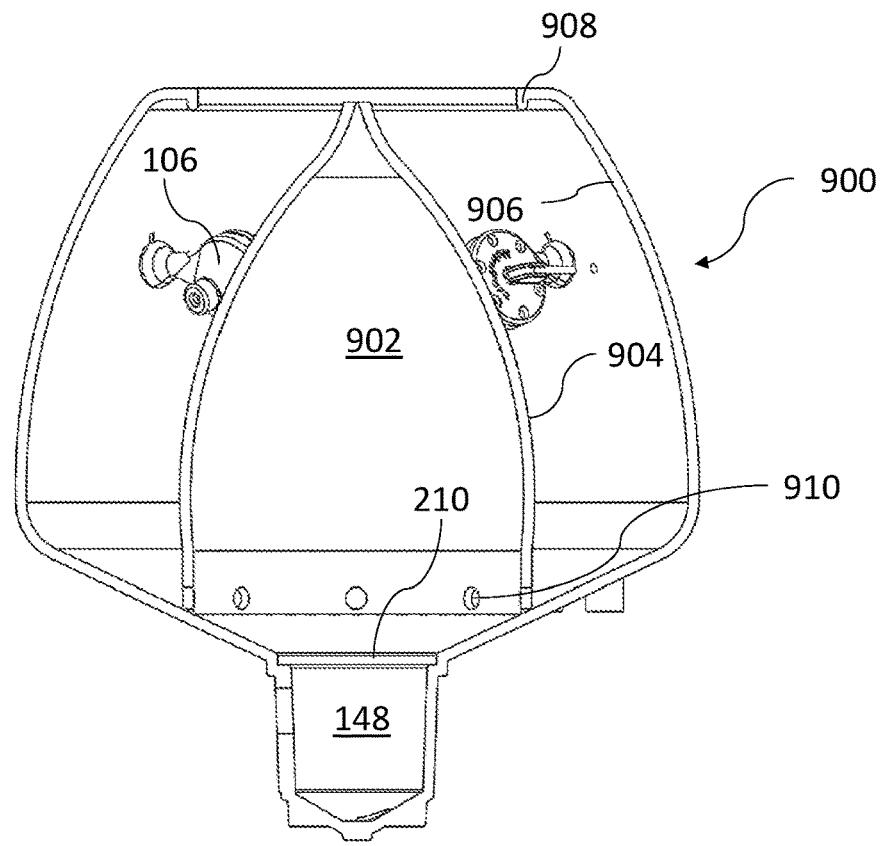
Figure 10A:
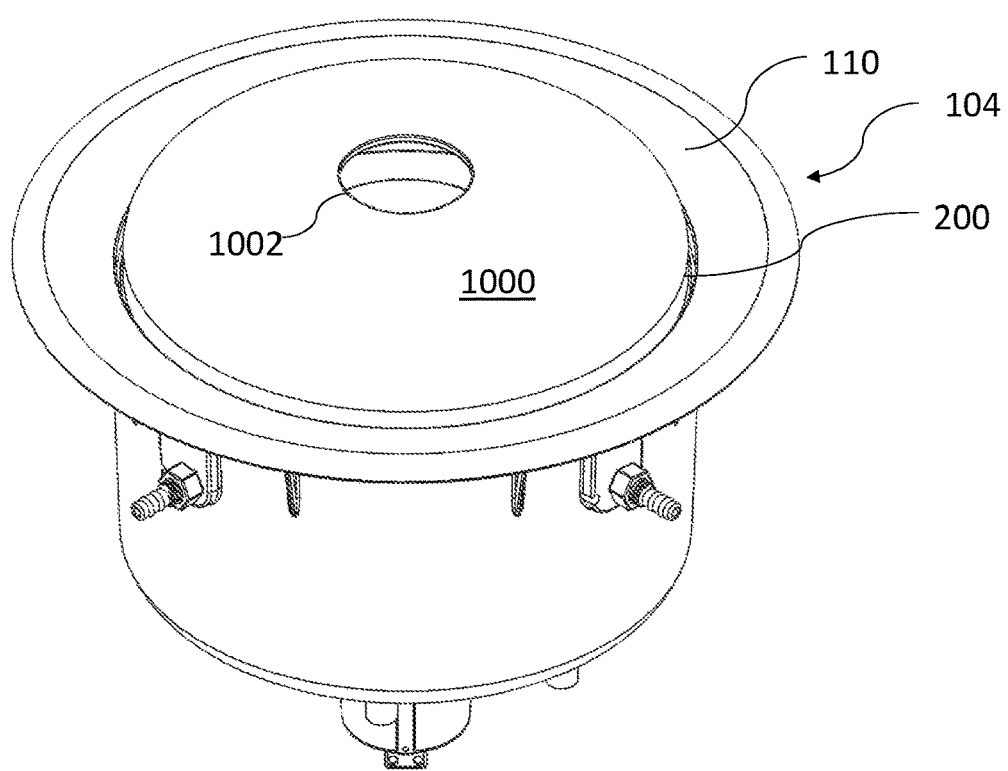
Figure 10B:
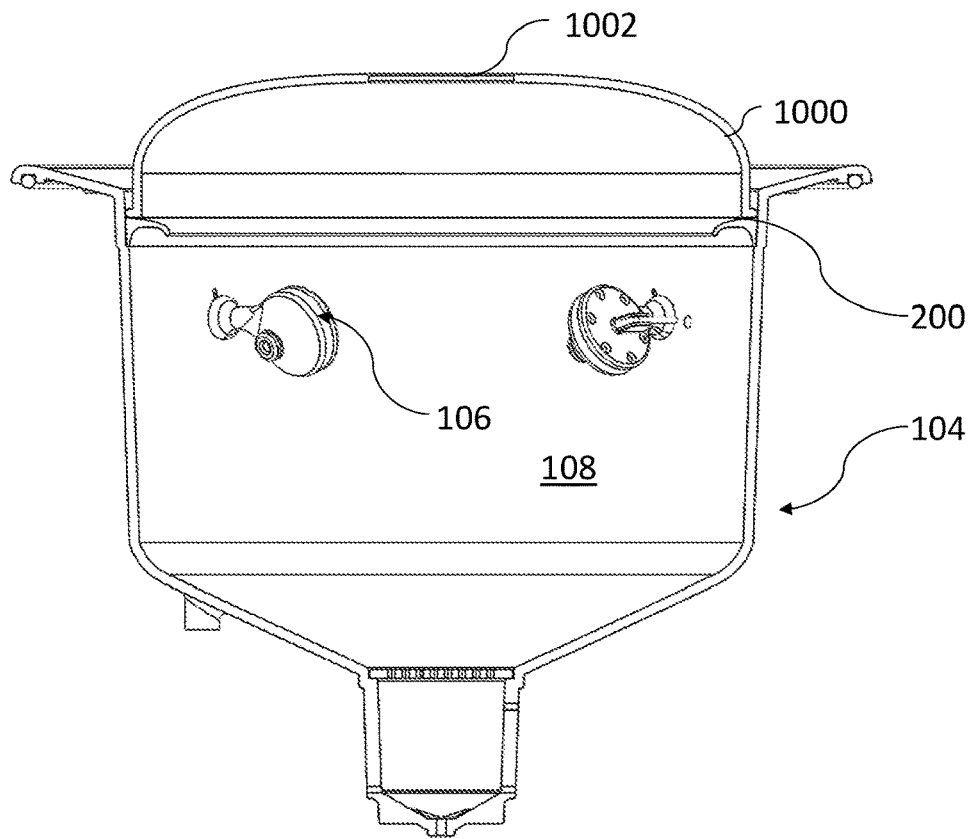
Figure 10C:
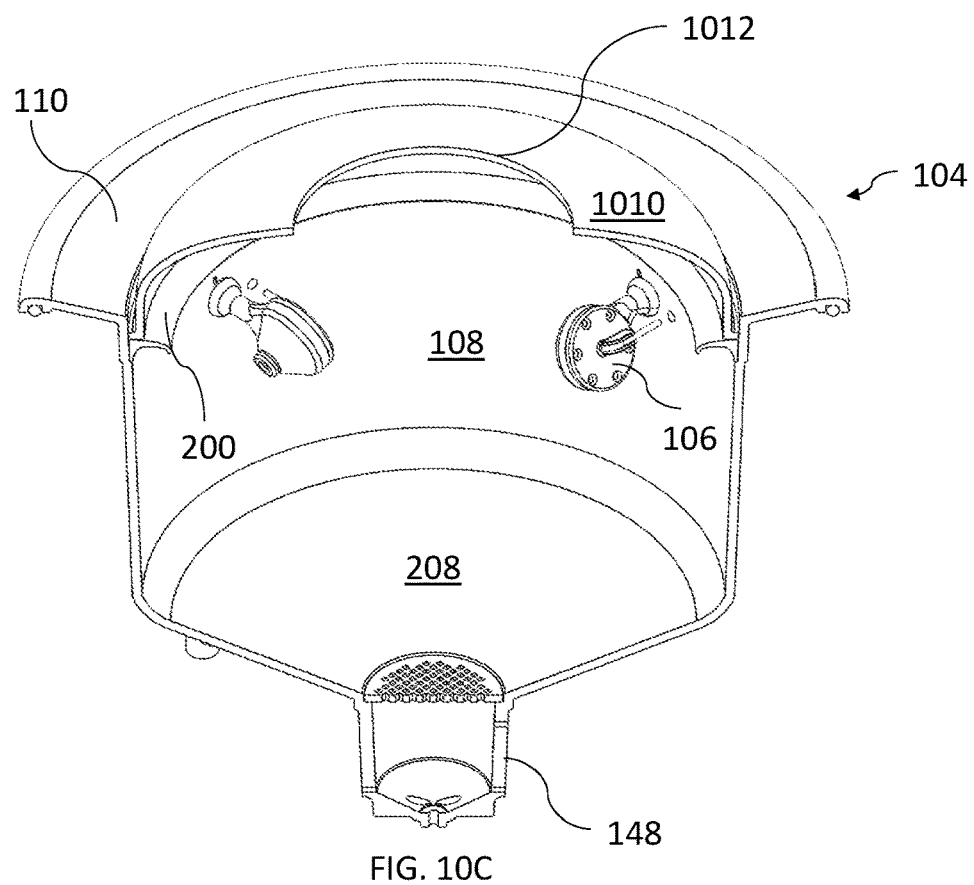

FIG. 8A depicts bowl 800 with central post 802 disposed within the bowl and having a continuous outer perimeter surface 804 defining an inner boundary of a flow volume within the bowl. All or part of post 802 may be cylindrical. A first end of post 802 proximate rim 110 of bowl 800 is closed. A second end of post 802 is in contact with the bottom of bowl 800. Nozzles 106 are disposed between side wall 108 of bowl and outer perimeter surface 804 of post 802. As the nozzles already create a rotating air flow within the bowl, the restricted space between side wall 108 of bowl 800 and outer perimeter surface 804 of post 802 causes higher velocities and therefore greater centrifugal forces on the aerosol. This increases the filtering out of the larger droplets both due to centrifugal forces while in bowl 800 and as the aerosol is forced to flow around lip 200.

FIG. 8B is a first cutaway view of bowl 800. Post 802 covers drain 210 of bowl 800. Apertures 806 in post 802 proximate drain 210 allow liquid flowing down side wall 108 and outer perimeter surface 804 of bowl 800 to drain into reservoir 148 for reuse. FIG. 8C is a second cutaway view of bowl 800, showing a hollow interior of post 802

FIG. 9A depicts bowl 900 with central post 902 disposed within the bowl and having a continuous outer perimeter surface 904 defining an inner boundary of a flow volume within the bowl. As depicted, outer perimeter surface 904 of post 902 is tapered, such that the post has a larger perimeter proximate the bottom of bowl 900. Side wall 906 of bowl 900 is tapered in a similar direction as outer perimeter surface 904 of post 902, such that the side wall generally follows the outer perimeter surface of the post. The tapered shape of post 902 and side wall 906 of bowl 900 forces rotating aerosol between the side wall and the post to spin faster as the airspace the aerosol flows within a smaller space as it nears lip 908 of the bowl. The faster rotation of the aerosol increases the filtering out of the larger droplets both due to centrifugal forces while in the bowl and as the aerosol is forced to flow around lip 908. FIG. 9B is a cutaway view of bowl 900 as depicted in FIG. 9A. Post 902 covers drain 210 of bowl 900. Apertures 910 in post 902 proximate drain 210 allow liquid flowing down outer perimeter surface 904 and side wall 906 to drain into reservoir 148 for reuse.

FIG. 10A depicts bowl 104 with lid 1000 defining central aperture 1002 to allow an aerosol to exit the bowl. In some implementations, lid 1000 contacts lip 200 of bowl 104. Lid 1000 provides additional filtering of the aerosol. Aperture 1002 may be of various sizes to provide different levels of filtering of the aerosol. In some implementations, lid 1000 is hingedly coupled to bowl 104 (e.g., to rim 110 of the bowl). In some implementations, lid 1000 slidably engages bowl 104. Lid 1000 protects nozzles disposed in bowl 104 and reduces dust and debris entering the bowl during operation or storage. FIG. 10B is a cutaway view of bowl 104 with lid 1000 defining aperture 1002. Lid 1000 is in contact with lip 200 of bowl 104. FIG. 10C is a cutaway view of bowl 104 with lid 1010 defining aperture 1012. Aperture 1012 of lid 1010 is larger in diameter than aperture 1002 of lid 1000.

Figure 11A:
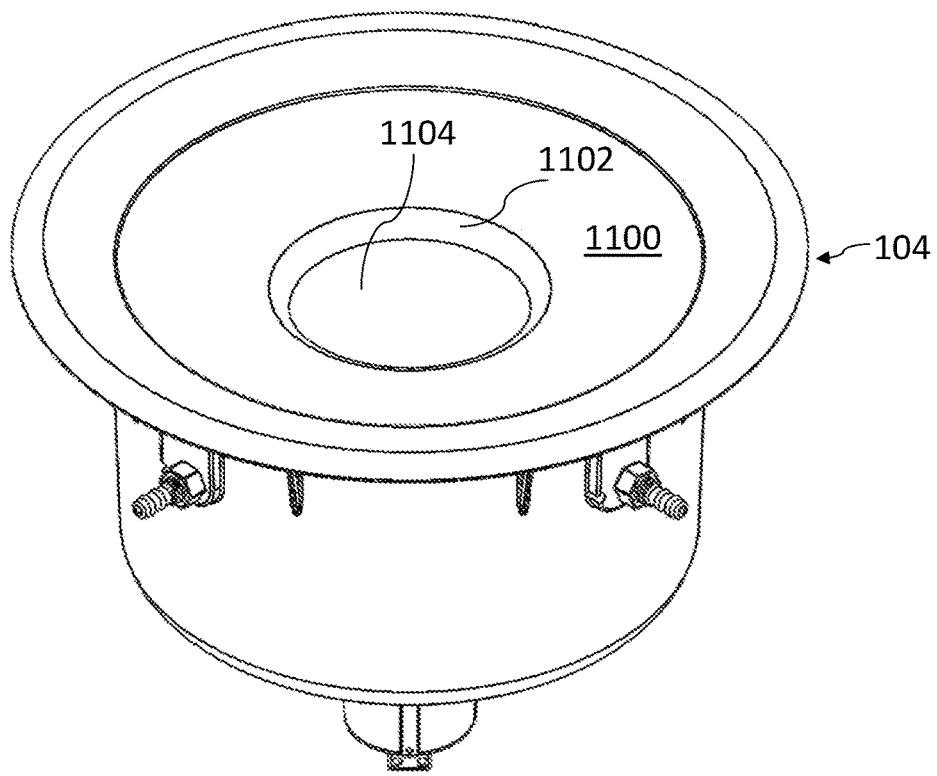
Figure 11B:
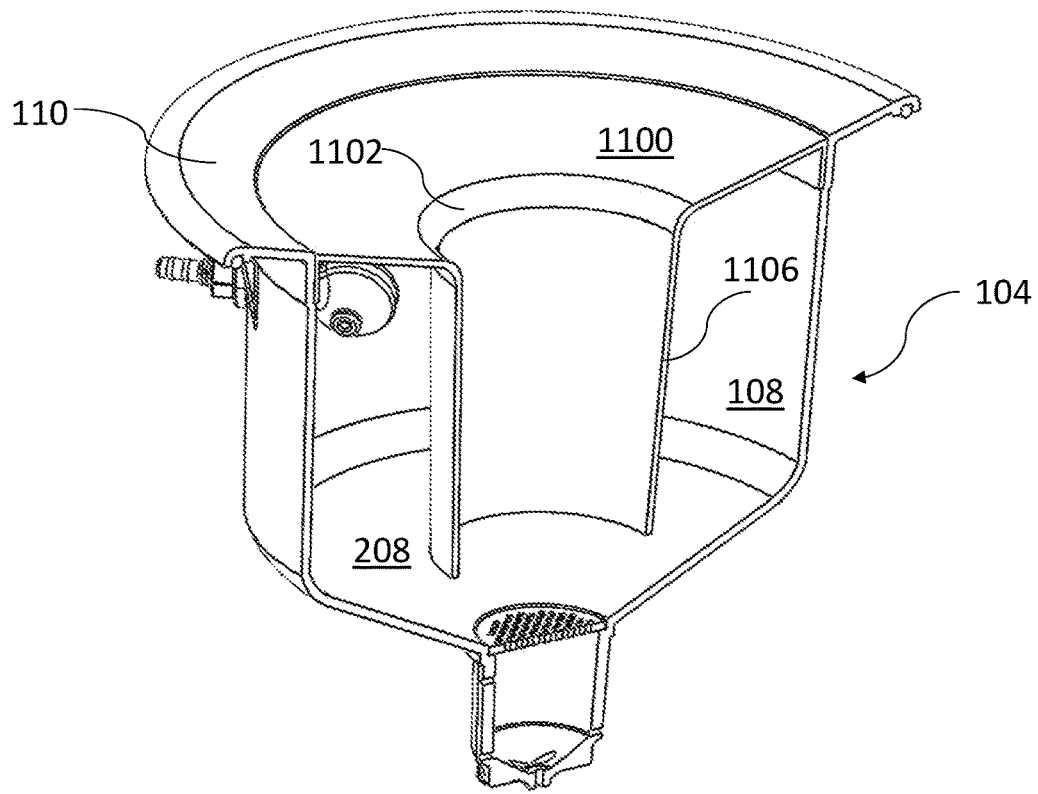
Figure 11C:
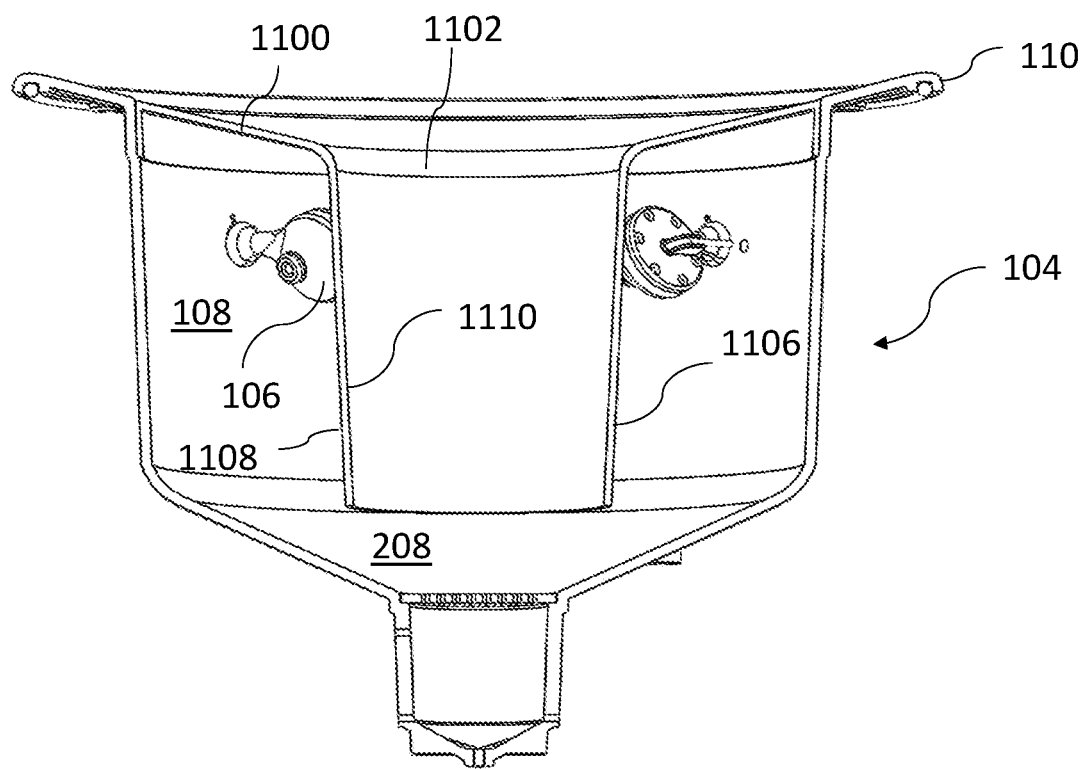

FIG. 11A depicts bowl 104 and lid 1100. Lid 1100 includes a central post having rim 1102 defining aperture 1104. FIG. 11B is a first cutaway view of bowl 104 with lid 1100 having post 1106. FIG. 11C is a second cutaway view of bowl 104 with lid 1100 having post 1106. Lid 1100 is coupled to side wall 108 proximate rim 110 of bowl 104, and post 1106 extends inwardly toward bottom 208 of the bowl. Post 1106 provides a filtering path for the rotating aerosol. Aerosol in bowl 104 is forced to flow between side wall 108 of bowl 104 and outer perimeter surface 1108 of post 1106. As nozzles 106 already create a rotating air flow within bowl 104, the restricted space between side wall 108 of the bowl and outer perimeter surface 1108 of post 1106 increases velocity and therefore increases centrifugal forces on the aerosol. After the aerosol reaches bottom 208 of bowl 104, the air flow carries the rotating aerosol up inner wall 1110 of post 1106. As the aerosol is now rotating in a smaller circle, the velocity increases further, again creating a filtering effect. In some implementations, post 1106 includes a lip, such as lip 200 depicted in FIG. 10B, for additional filtering.

Figure 12:
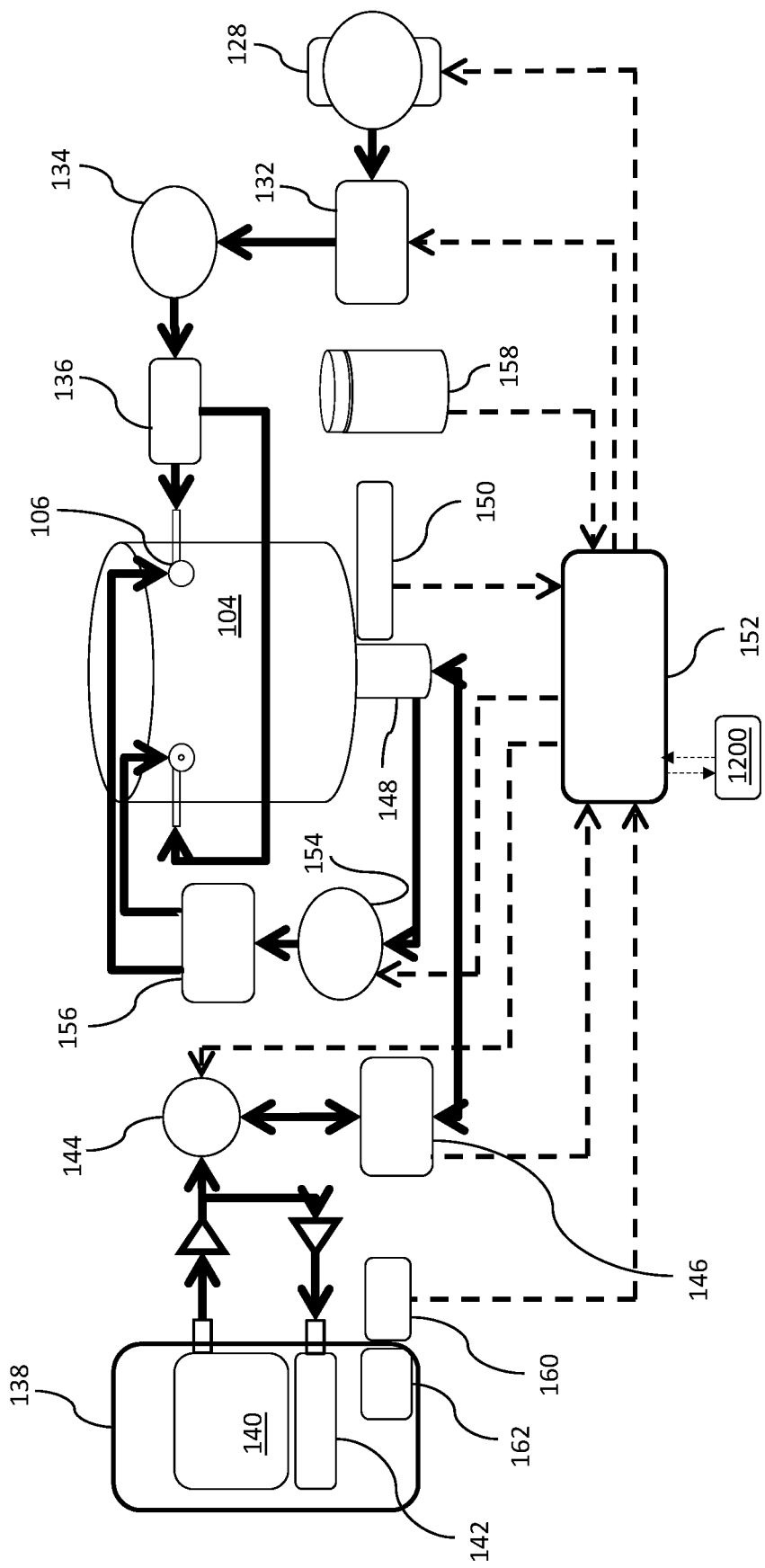
Figure 13:
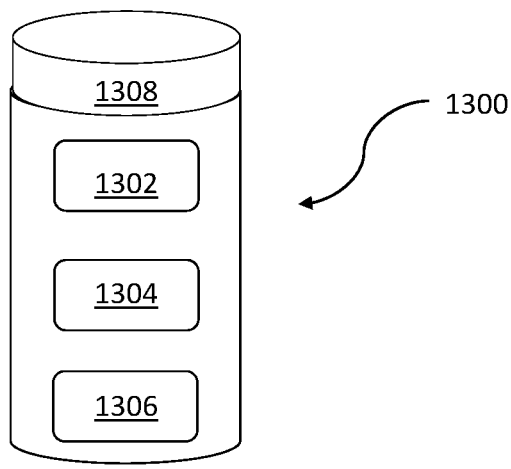

FIG. 12 is a flow diagram depicting a process flow for an aerosol device including a processor. As depicted in FIG. 12, processor 152 receives input from liquid sensors 146, liquid level sensor 150, air sensors 158, and RFID sensor 160, and provides input to pressurized gas source 128, air pressure (or air flow) regulator 132, reversible pump 144, and recirculation pump 154. In some implementations, air sensors 158 are arranged in a sensor tube. FIG. 13 depicts sensor tube 1300 including relative humidity sensor 1302, temperature sensor 1304, and barometric pressure sensor 1306. In some implementations, sensor tube 1300 includes fan 1308 that draws air from a target volume such that the air contacts sensors 1302, 1304, 1306 in the sensor tube. Processor 152 may control generation of an aerosol (e.g., duration of aerosol generation) by controlling one or more of pressurized gas source 128, air pressure (or air flow) regulator 132, reversible pump 144, and recirculation pump 154 based on input received from one or more of liquid sensors 146, liquid level sensor 150, air sensors 158, and RFID sensor 160, and provides input to pressurized gas source 128, air pressure (or air flow) regulator 132, reversible pump 144, and recirculation pump 154. Processor is operatively coupled to memory 1200.

Figure 14:
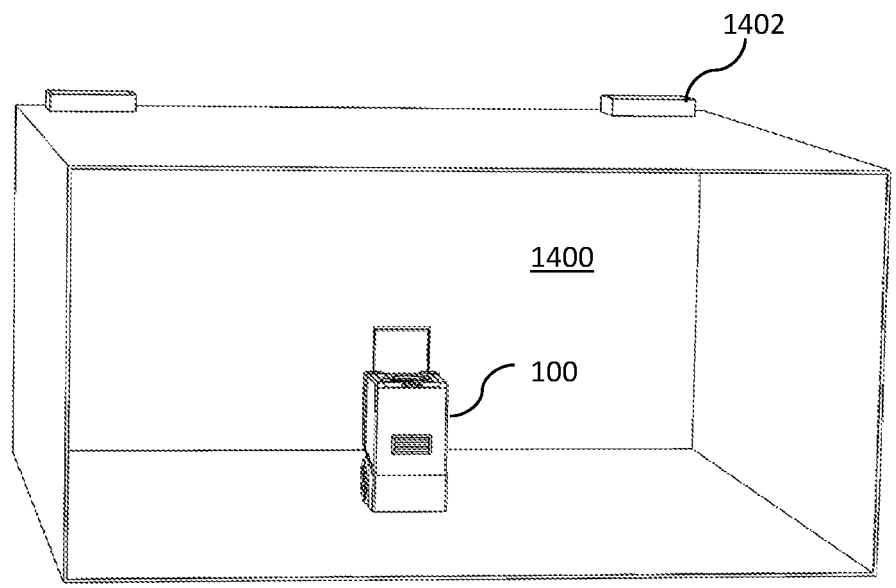

In one example, an aerosol device may be used to automatically disinfect a target volume. Examples of target volumes include enclosed volumes, such as automobiles, boats, aircraft, trains, crawlspaces, and tunnels, and rooms of various sizes. FIG. 14 depicts aerosol device 100 disposed within target volume 1400 having vents 1402. Outside air exchanged into a target volume (e.g., through vents 1402) while aerosol generation is in progress may affect the time needed for an aerosol device to effectively treat the target volume. The air being exchanged with a target volume effectively increases its volume. This effective volume is a factor in determining the duration of an effective treatment.

As used herein, "effective volume" is the actual size of the target volume plus the air exchanged into the target volume during the treatment. For example, for a 1 hour treatment, a 100 cubic meter target volume with an air exchange per hour equal to the target volume has an effective volume of 200 cubic meters. For treatments that rely on a concentration of a substance, such as disinfectant, a treatment may be based on an effective volume of the target volume rather than on the target volume. Treatment of a target volume based on its effective volume may be achieved as described herein, through monitoring and analysis of environmental conditions.

Assessing the effective volume of a target volume includes monitoring temperature, barometric pressure, and relative humidity of the target volume. Assessing the effective volume of a target volume may be implemented for treatments that rely on diffusion of an aerosol within the target volume, and also has applicability to fogging, spray, or misting systems in which an aqueous liquid is used. Temperature, barometric pressure, and relative humidity sensors can be located in the target volume or in or on the treatment device, such as an aerosol device.

The percent relative humidity (RH %) increase in a target volume during treatment by an aerosol device will generally follow the saturation curve $W+(1-e^{-X})$. The value of X varies based on the volume of the target volume, the air exchange rate into the target volume, the performance characteristics of the aerosol device, and environmental variables. W is the starting RH % value of a target volume. For illustrative purposes, a standard volume may be defined as 50 cubic meters ($m^3$). However, a standard volume is not limited to this volume, and may have other values. The standard volume is sealed, with an aerosol device inside, to prevent air exchange. The standard volume simplifies operations made by an aerosol device to assess an effective volume. A lookup table or matrix provides the RH % standard volume curve exponent (X) for each combination of temperature, RH %, and barometric pressure. The lookup table or function may also retrieve other variables based on values of RH %, temperature, and barometric pressure. These variables may be used to alter operation or performance of an aerosol device. For example, the variable may, for certain conditions of temperature, RH %, and barometric pressure, instruct the operator to turn off a HVAC unit in the target volume.

The lookup table may be stored in memory of an aerosol device. The RH % standard volume curve exponent is empirically derived from testing across the expected operational ranges of temperature, barometric pressure, RH %, target volume, and air exchange rates. This data is stored in memory accessible by the processor. The stored data includes the lookup table of RH % standard volume curve exponents for a standard volume for a range of RH %, temperature, and barometric pressure values. In some implementations, a separate scaling function is used for barometric pressure to adjust the RH % standard volume curve exponent after lookup in the table. Barometric pressure data may become significant at high altitudes. In some implementations, each of RH %, temperature, and barometric pressure may be stored as a function separately or together instead of a lookup table. Data in the lookup tables can be interpolated to increase accuracy. The stored data may also include a RH % limit value which, if exceeded during a treatment, may result in condensation.

At the start of a treatment, an initial time is noted, and temperature, relative humidity, and barometric pressure measurements are taken. Multiple samples of each metric may be averaged to increase the accuracy of the measurements.

The RH % standard volume curves stored in the lookup table supply the exponent (X) of the RH % standard volume curve. The RH % standard volume curve follows the format $W+(1-W)(1-e^{-X})$ where W is the initially measured RH % and X is the RH % standard volume curve exponent. Other formulas for RH % may also be used. The RH % standard volume curve provides the expected RH % curve for a treatment in a standard volume (e.g., 50 m$^3$) with the current RH %, temperature, and barometric pressure. If RH % is above the RH % limit, aerosol is not dispensed.

During treatment, time and RH % are monitored and recorded. As temperature and barometric pressure are unlikely to change significantly over the course of a treatment (and as seen in testing), temperature and barometric pressure may be considered fixed after the initial measurement. RH % measurements may be monitored once every 10 seconds or more frequently if averaging of the values is used to increase accuracy. If RH % is above the RH % limit, aerosol is not dispensed.

After an elapsed time (e.g., 5 minutes), the processor fits the recorded RH % values, including the initial RH % value, to a curve with the format $W+Y(1-e^{-Z})$ where W is the initial measured RH % value and Y and Z are unknown. W is the initial measured RH % value, Y is the maximum RH % rise for the effective volume, and Z is the RH % effective volume exponent. The formula, $W+Y(1-e^{-Z})$, defines a curve that is the RH % effective volume curve. It estimates the RH % curve for the effective volume and is an estimate of how RH % will increase in the target volume (different than the RH % standard volume curve which represents RH % increase in a standard volume). At each regularly spaced curve fit, the values for W, Y and Z are recorded.

The number of data points to fit can be reduced to lessen processor workload. If points are reduced, averaging local points around the chosen points should be considered. A least-squares curve fit method may be appropriate as events such as outside air exchange systems cycling may make exact curve fitting difficult. Other appropriate curve fit methods can be used to find the best fit to the formula.

The effective volume is the standard volume (e.g., 50 m$^3$) multiplied by the RH % effective volume exponent (Z) divided by the RH % standard volume exponent (X). Once the effective volume is known, treatment time may be determined based on the effective volume. A maximum humidity of the target volume can be obtained from the initial measured RH % (W) added to the maximum RH % rise for the effective volume (Y). A low maximum humidity (typically under 70%) for the target volume is an indicator that additional aerosol devices may be utilized in the room at the same time to speed up treatment without approaching the RH % limit.

FIG. 15 is a flow chart showing process 1500 for treating a target volume or room as described herein. 1502 includes assessing an initial relative humidity, an initial ambient temperature, and an initial barometric pressure in a room. 1504 includes initiating production of an aerosol within the room. 1506 includes monitoring the relative humidity within the room over time to yield measured values of relative humidity as a function of time. 1508 includes comparing the measured values of relative humidity with stored reference data. The stored reference data may include known values of relative humidity as a function of time for a reference room of a known volume in which a reference aerosol is generated at a known initial relative humidity, a known initial ambient temperature, and a known initial barometric pressure. 1510 includes, based on the comparison, determining a treatment parameter of the aerosol in the room. 1512 includes terminating production of the aerosol within the room after the treatment parameter has been achieved. In some implementations, the treatment parameter includes at least one of a total production time of the aerosol, a total amount of a disinfectant in the aerosol, and a target relative humidity percentage in the room.

FIG. 16 is a flow chart showing process 1600 for disinfecting a room. In 1602, an aerosol is provided to a room. The aerosol is generated by an aerosol device as described herein. The aerosol device may be within the room, as depicted in FIG. 14, or positioned outside of the room. The aerosol may be generated within the room, or generated outside of the room and subsequently provided to the room. The aerosol includes liquid droplets, and the liquid droplets include a disinfectant. A majority of the liquid droplets have a maximum dimension in a range between 0.01 μm and 0.07 μm. In 1604, the liquid droplets are allowed to diffuse throughout the room and into porous articles in the room for a sufficient length of time to disinfect the room. The time to disinfect the room may be determined automatically as described herein.

Figure 17:
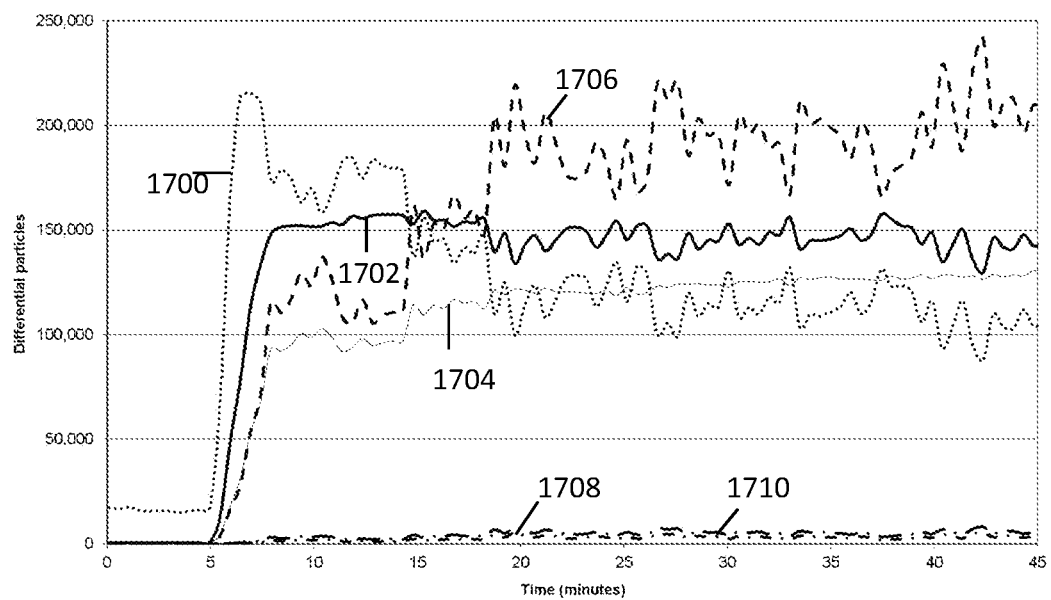

FIG. 17 shows particle size distribution by size range of liquid droplets generated by an aerosol device as described herein. Plots 1700, 1702, 1704, 1706, 1708, and 1710 show a number of particles having a maximum dimension in a range of 0.3 μm to 0.5 μm, 0.5 μm to 0.7 μm, 0.7 μm to 1.0 μm, 1.0 μm to 3.0 μm, 3.0 μm to 5.0 μm, and >0.5 μm, respectively, for up to 45 minutes. Most of the particles have a maximum dimension of less than 3.0 μm.

Figure 18:
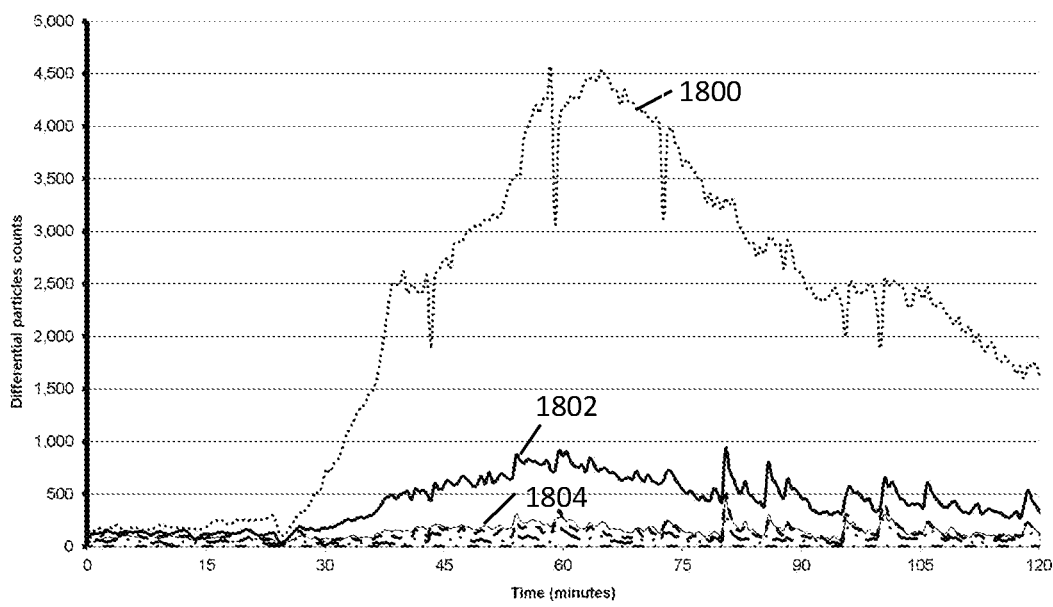

FIG. 18 shows particle size distribution by size range of liquid droplets that penetrated through multiple layers of cloth. Plots 1800 and 1802 show a number of particles having a maximum dimension in a range of 0.3 μm to 0.5 μm and 0.5 μm to 0.7 μm, respectively, that penetrate through the cloth over 120 minutes. Particles having a maximum dimension a range of 0.7 μm to 1.0 μm are shown as plot 1804, and particles having a maximum dimension greater than 1.0 μm are shown as superimposed plots that fall below plot 1804. Thus, only the droplets having a maximum particle size up to 0.7 μm penetrate through multiple layers in a manner effective to disinfect the cloth. This was in contrast with the pore size of the cloth, which was estimated to be significantly larger holes than 0.7 μm. Thus, particles having a maximum dimension of greater than 0.7 μm are not effective in penetrating cloth, and therefore not effective in disinfecting the cloth. Droplets having a maximum dimension of less than 0.1 μm are considered to have a mass concentration of disinfectant too low to achieve any significant disinfection of the cloth. As such, particles having a maximum dimension in a range between 0.1 μm and 0.7 μm are considered to be effective to achieve disinfection of porous articles having pores, openings, or air gaps, including pores, openings, or air gaps having a dimension larger than 0.7 μm. Examples of such pores, openings, and airgaps include gaps and pores in concrete, particle board, grout lines, and air gaps between the weave in carpeting. As depicted in FIG. 18, particles having a maximum dimension in a range between 0.3 μm and 0.7 μm are also effective to achieve disinfection of porous articles having pores, openings, or air gaps, including pores, openings, or air gaps having a dimension larger than 0.7 μm.

Thus, particular implementations of the subject matter have been described. Other implementations are within the scope of the claims.

What is claimed is:

1. An aerosol device, comprising:
a bowl with a bottom defining a drain, and a side wall extending from the bottom to a rim, wherein the bottom and the side wall together define an interior surface of the bowl bounding a bowl volume;
a nozzle disposed within the bowl, the nozzle defining a chamber and an outlet orifice directed toward the side wall of the bowl;
a liquid container fluidly coupled to the nozzle via a first conduit having an outlet tip disposed within the chamber of the nozzle; and
a second conduit connecting a source of pressurized gas to the chamber of the nozzle;
wherein the outlet tip is in the form of a tube defining elongated slots communicating from inside the tube to outside the tube, the slots each having a width defined between two parallel tube surfaces,
wherein each of the slots has at least one end formed by two square corners.

2. An aerosol device, comprising:
a bowl with a bottom defining a drain, and a side wall extending from the bottom to a rim, wherein the bottom and the side wall together define an interior surface of the bowl bounding a bowl volume;
a nozzle disposed within the bowl, the nozzle defining a chamber and an outlet orifice directed toward the side wall of the bowl;
a liquid container fluidly coupled to the nozzle via a first conduit having an outlet tip disposed within the chamber of the nozzle; and
a second conduit connecting a source of pressurized gas to the chamber of the nozzle;
wherein the outlet tip is in the form of a tube defining elongated slots communicating from inside the tube to outside the tube, the slots each having a width defined between two parallel tube surfaces,
wherein each of the slots has at least one end formed by a radius.

3. An aerosol device, comprising:
a bowl with a bottom defining a drain, and a side wall extending from the bottom to a rim, wherein the bottom and the side wall together define an interior surface of the bowl bounding a bowl volume;
a nozzle disposed within the bowl, the nozzle defining a chamber and an outlet orifice directed toward the side wall of the bowl;
a liquid container fluidly coupled to the nozzle via a first conduit having an outlet tip disposed within the chamber of the nozzle; and
a second conduit connecting a source of pressurized gas to the chamber of the nozzle;
wherein the outlet tip is in the form of a tube defining elongated slots communicating from inside the tube to outside the tube, the slots each having a width defined between two parallel tube surfaces,
wherein each of the slots has two closed ends.

4. An aerosol device, comprising:
a bowl with a bottom defining a drain, and a side wall extending from the bottom to a rim, wherein the bottom and the side wall together define an interior surface of the bowl bounding a bowl volume;
a nozzle disposed within the bowl, the nozzle defining a chamber and an outlet orifice directed toward the side wall of the bowl;
a liquid container fluidly coupled to the nozzle via a first conduit having an outlet tip disposed within the chamber of the nozzle; and
a second conduit connecting a source of pressurized gas to the chamber of the nozzle;
wherein the outlet tip is in the form of a tube defining elongated slots communicating from inside the tube to outside the tube, the slots each having a width defined between two parallel tube surfaces,
wherein each of the slots is open at an end of the tube.

5. An aerosol device, comprising:
a bowl with a bottom defining a drain, and a side wall extending from the bottom to a rim, wherein the bottom and the side wall together define an interior surface of the bowl bounding a bowl volume;
a nozzle disposed within the bowl, the nozzle defining a chamber and an outlet orifice directed toward the side wall of the bowl;
a liquid container fluidly coupled to the nozzle via a first conduit having an outlet tip disposed within the chamber of the nozzle; and
a second conduit connecting a source of pressurized gas to the chamber of the nozzle;
wherein the outlet tip is in the form of a tube defining elongated slots communicating from inside the tube to outside the tube, the slots each having a width defined between two parallel tube surfaces,
wherein each of the slots defines a longitudinal axis parallel with a longitudinal axis of the tube.

6. An aerosol device, comprising:
a bowl with a bottom defining a drain, and a side wall extending from the bottom to a rim, wherein the bottom and the side wall together define an interior surface of the bowl bounding a bowl volume;
a nozzle disposed within the bowl, the nozzle defining a chamber and an outlet orifice directed toward the side wall of the bowl;
a liquid container fluidly coupled to the nozzle via a first conduit having an outlet tip disposed within the chamber of the nozzle; and
a second conduit connecting a source of pressurized gas to the chamber of the nozzle;
wherein the outlet tip is in the form of a tube defining elongated slots communicating from inside the tube to outside the tube, the slots each having a width defined between two parallel tube surfaces,
wherein a length of each of the slots forms an acute angle with a longitudinal axis of the tube.

* * * * *